US012521250B2

(12) United States Patent
Grabinsky et al.

(10) Patent No.: US 12,521,250 B2
(45) Date of Patent: Jan. 13, 2026

(54) MEDICAL IMPLANT DELIVERY SYSTEM

(71) Applicants: Smith & Nephew, Inc., Memphis, TN (US); Smith & Nephew Orthopaedics AG, Zug (CH); Smith & Nephew Asia Pacific Pte. Limited

(72) Inventors: Jessica M. Grabinsky, Mansfield, MA (US); David A. Yeung, Andover, MA (US); Francheska Torres, Charlton, MA (US); Kevin M. Falco, Andover, MA (US)

(73) Assignees: Smith & Nephew, Inc.; Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 548 days.

(21) Appl. No.: 17/942,586

(22) Filed: Sep. 12, 2022

(65) Prior Publication Data

US 2023/0021001 A1 Jan. 19, 2023

Related U.S. Application Data

(63) Continuation of application No. PCT/US2021/025403, filed on Apr. 1, 2021.

(Continued)

(51) Int. Cl.

| | |
|---|---|
| ***A61F 2/08*** | (2006.01) |
| ***A61F 2/40*** | (2006.01) |
| *A61F 2/00* | (2006.01) |

(52) U.S. Cl.

CPC .................. *A61F 2/40* (2013.01); *A61F 2/08* (2013.01); *A61F 2002/0072* (2013.01)

(58) Field of Classification Search

CPC ............ A61F 2/0063; A61F 2002/0072; A61F 2/0805; A61F 2/40; A61B 17/3468; A61B 17/50; A61B 17/29–17/295

See application file for complete search history.

(56) References Cited

U.S. PATENT DOCUMENTS 5,575,805 A * 11/1996 Li .......................... A61B 17/29 606/174
7,648,514 B1 * 1/2010 Nakao ................. A61B 17/064 606/151

(Continued)

FOREIGN PATENT DOCUMENTS

CA 2909960 A1 4/2016
CN 110381860 A 10/2019

(Continued)

OTHER PUBLICATIONS

International Search Report and Written Opinion dated Sep. 7, 2021 for International Application No. PCT/US2021/025403.

*Primary Examiner* — Kathleen S Holwerda
(74) *Attorney, Agent, or Firm* — Seager, Tufte & Wickhem LLP

(57) ABSTRACT

Implant delivery systems are disclosed. One implant delivery system includes an outer shaft, an inner shaft movable within the outer shaft, a yoke coupled to the distal end of the inner shaft, and an implant retainer pivotably coupled to the yoke. The implant retainer is configured to retain a sheet-like implant for implantation at a treatment site. Another implant delivery system includes a handle, a delivery sheath extending from the handle, and a delivery shaft extending through the delivery sheath to a frame attachable to a sheet-like implant. A tether extends from the frame within the lumen of the delivery shaft. An actuation member is translatable within a channel of the handle to deploy the frame from the delivery sheath. A tether clamp, positioned within the (Continued)

handle, is manipulatable by the actuation member to selectively unlock the tether within the handle.

13 Claims, 25 Drawing Sheets

Related U.S. Application Data

(60) Provisional application No. 63/004,638, filed on Apr. 3, 2020, provisional application No. 63/004,667, filed on Apr. 3, 2020.

(56) References Cited

U.S. PATENT DOCUMENTS

| | | | |
|---|---|---|---|
| 8,864,780 B2 | 10/2014 | Euteneuer et al. | |
| 8,906,045 B2 | 12/2014 | Levin et al. | |
| 10,028,814 B2 | 7/2018 | Levin et al. | |
| 10,258,459 B2 | 4/2019 | Zenz-Olson | |
| 2011/0040311 A1 | 2/2011 | Levin et al. | |
| 2012/0209401 A1* | 8/2012 | Euteneuer | A61F 2/0805 623/23.72 |
| 2018/0333246 A1 | 11/2018 | Levin et al. | |
| 2019/0110885 A1 | 4/2019 | Zenz-Olson et al. | |

FOREIGN PATENT DOCUMENTS

| | | |
|---|---|---|
| WO | 2013101638 A1 | 7/2013 |
| WO | 2013101640 A1 | 7/2013 |

* cited by examiner

MEDICAL IMPLANT DELIVERY SYSTEM

CROSS REFERENCE TO RELATED APPLICATIONS

This application is a continuation of International Application No. PCT/US2021/025403, filed Apr. 1, 2021, titled MEDICAL IMPLANT DELIVERY SYSTEM AND RELATED METHODS, which claims the benefit of and priority to U.S. Provisional Patent Application Ser. No. 63/004,638, filed on Apr. 3, 2020, titled PIVOTING CENTRAL BEAM FOR NEXTGEN SCAFFOLD DELIVERY, and U.S. Provisional Patent Application Ser. No. 63/004,667, filed on Apr. 3, 2020, titled ROTATIONAL LOCKING/UNLOCKING MECHANISM FOR ARTHROSCOPIC DELIVERY DEVICE, the disclosures of which are incorporated herein by reference.

TECHNICAL FIELD

The present disclosure pertains generally, but not by way of limitation, to orthopedic implants, implant delivery systems, and methods of treatment. More particularly, the present disclosure relates to a tendon repair implant delivery device for arthroscopic placement of a sheet-like tissue implant over or in the area of a full or partial thickness tear of a tendon, such as the supraspinatus tendon of the shoulder

BACKGROUND

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. There is an ongoing need to deliver and adequately position medical implants during an arthroscopic procedure in order to treat injuries to the rotator cuff, rotator cuff tendons, or other soft tissue or tendon injuries throughout a body.

BRIEF SUMMARY

This disclosure provides design, material, manufacturing method, and use alternatives for medical devices.

A first example includes an implant delivery system. The implant delivery system includes an outer shaft having a proximal end, a distal end and lumen extending therein. The implant delivery system also includes an inner shaft including a proximal end and a distal end. The inner shaft extends within a least a portion of the lumen of the outer shaft. A yoke is coupled to the distal end of the inner shaft. An implant retainer is coupled to the yoke. The implant retainer is configured to capture an implant. The implant retainer is configured to pivot relative to the yoke.

Additionally or alternatively to any example above, the implant delivery system further includes a spring component coupled to both the yoke and the implant retainer.

Additionally or alternatively to any example above, the spring component includes a first end and a second end, wherein the first end is fixedly attached to the yoke, and wherein the second end extends away from the yoke and is positioned within an internal bore located on the implant retainer.

Additionally or alternatively to any example above, the spring component includes a first end and a second end, wherein the first end is fixedly attached to the implant retainer, and wherein the second end extends away from the implant retainer and is positioned within an internal bore located on the yoke.

Additionally or alternatively to any example above, the spring component is configured to flex between a first position in which it is aligned with a longitudinal axis of the yoke and a second position in which it is offset from the longitudinal axis of the yoke.

Additionally or alternatively to any example above, the spring component is configured to bias the implant retainer in the second position after the implant is deployed from the lumen of the outer shaft.

Additionally or alternatively to any example above, the implant retainer includes an upper beam coupled to a lower beam, and wherein the implant is captured between the upper beam and the lower beam.

Additionally or alternatively to any example above, the lower beam includes a spring component coupled to the upper beam, and wherein the spring component includes a proximal end portion which extends into a bore of the yoke.

Additionally or alternatively to any example above, the yoke includes a first longitudinal arm spaced away from a second longitudinal arm, and wherein the first longitudinal arm includes a first recess configured to accept a first projection positioned on the implant retainer, and wherein the second longitudinal arm includes a second recess configured to accept a second projection positioned on the implant retainer.

Additionally or alternatively to any example above, the first projection is configured to pivot within the first recess and wherein the second projection is configured to pivot within the second recess.

Another example includes an implant delivery system. The implant delivery system includes a handle having a distal end region, a proximal end region and a channel extending from the distal end region to the proximal end region. A delivery sheath extends distally from the handle. The delivery sheath has a lumen extending to a distal end of the delivery sheath. A delivery shaft is positioned in the lumen of the delivery sheath. The delivery shaft has a distal end, a proximal end and a lumen extending therein. A frame is coupled to the distal end of the delivery shaft. The frame is attachable to a sheet-like implant. An actuation member is translatable within the channel to deploy the frame from the delivery sheath. A tether extends from the frame within the lumen of the delivery shaft and at least a portion of the handle. A tether clamp is positioned within the handle. The tether clamp is manipulatable by the actuation member to selectively unlock the tether within the handle.

Additionally or alternatively to any example above, unlocking the tether clamp permits the tether to translate with respect to the handle, the delivery shaft or both the handle and the delivery shaft.

Additionally or alternatively to any example above, translating the actuation member from a distal end region of the channel to a proximal end region of the channel shifts the delivery sheath in a proximal direction relative to the delivery shaft from a first position to a second position.

Additionally or alternatively to any example above, the tether clamp includes a locking lever designed to rotate between a first position in which the lever locks the tether to the handle and a second position in which the tether is free to translate with respect to the handle.

Additionally or alternatively to any example above, the actuation member further includes an engagement member configured to engage the locking lever, and wherein rotation of the actuation member engages the engagement member with the lever such that the lever rotates from the first position in which the lever locks the tether to the handle to the second position in which the tether is free to translate with respect to the handle.

Additionally or alternatively to any example above, the tether clamp includes a moving component positioned adjacent to a fixed component, wherein the moving component is designed to move between a first position in which the tether is locked between the moving component and the fixed component, and a second position in which the tether is free to translate with respect to the moving component and the fixed component.

Additionally or alternatively to any example above, a spring is attached to the moving component. The spring is configured to apply a force to the moving component to lock the tether between the moving component and the fixed component.

Additionally or alternatively to any example above, the actuation member further includes an engagement member configured to engage the moving component, and wherein rotation of the actuation member engages the engagement member with the moving component such that the moving component translates between the first position in which the moving component locks the tether to the handle and the second position in which the tether is free to translate with respect to the moving component and the fixed component.

Additionally or alternatively to any example above, the tether clamp includes a locking block including a slot extending between adjacent first and second sidewalls of the locking block through which the tether extends, and an engagement feature designed to engage a mating engagement feature of the actuation member. The first sidewall of the locking block is configured to move relative to the second sidewall of the locking block between a first position in which the tether is pressed between the first and second sidewalls and a second position in which the tether is free to translate within the slot. Additionally or alternatively to any example above, rotation of the actuation member rotates the first sidewall between the first position in which the tether is locked within the slot of the locking block and the second position in which the tether is free to translate within the slot.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
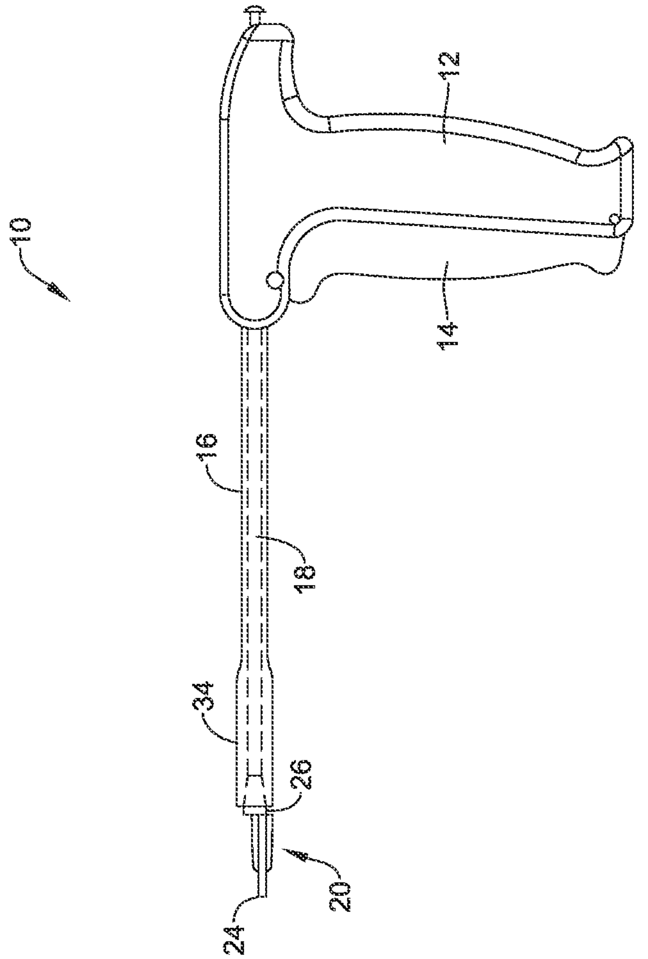
FIG. 1 illustrates an example implant delivery system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. An accepted treatment for rotator cuff tears may include reattaching the torn tendon to the humeral head using sutures. Additionally, in treating rotator cuff tears, an accepted practice may also include the placement of a scaffold over the repaired tendon to mechanically reinforce the repaired tendon and/or promote tissue reformation. Therefore, there is an ongoing need to deliver and adequately position medical implants during an arthroscopic procedure in order to treat injuries to the rotator cuff, rotator cuff tendons, or other soft tissue or tendon injuries throughout a body.

FIG. 1 shows an example implant delivery system 10. The example implant delivery system 10 may include a handle 12 having a trigger 14. Additionally, the implant delivery system 10 may include an outer shaft 16 coupled to the handle 12. Further, FIG. 1 illustrates that the implant delivery system 10 may include an inner shaft 18 extending within the outer shaft 16. The implant delivery system 10 may also include an implant delivery device assembly 20 coupled to the distal end region of the inner shaft 18 via a yoke 26. The implant delivery device assembly 20 may include a swivel arm 25 coupled to an implant 24.

The outer shaft 16 of the implant delivery system 10 may include a proximal end (attached to the handle 12), a distal end and a lumen extending within at least a portion of the outer shaft 16. In some examples, the distal end of the outer shaft 16 may be attached to a delivery sheath 34. In other words, the delivery sheath 34 may extend away from the distal end of the outer shaft 16 whereby the distal end of the outer shaft 16 may be attached to a proximal end of the delivery sheath 34. In some examples, the delivery sheath 34 may resemble a substantially cylindrical sheath, a portion of which may be over-molded onto the distal end of the outer shaft 16. The delivery sheath 34 may be designed to house the implant delivery device assembly 20 (including the implant 24) in a rolled, folded or otherwise collapsed delivery state as the implant delivery system 10 accesses a target site.

For clarity, FIG. 1 illustrates the implant delivery device assembly 20 extending out of the distal end of the delivery sheath 34. It can be appreciated that the implant delivery device assembly 20 may be positioned within the lumen of the delivery sheath 34 prior to being deployed out of the distal end of the delivery sheath 34. For example, the implant delivery device assembly 20 (including the implant 24) may be positioned in a rolled, folded or otherwise collapsed delivery configuration within the lumen of the delivery sheath 34 while being tracked to a target site.

It can be further appreciated that actuation of the trigger 14 may shift the outer shaft 16 relative to both the implant assembly 20 and the inner shaft 18. For example, actuation of the trigger 14 may shift the outer shaft 16 between a first position in which the implant assembly 20 is positioned within the lumen of the delivery sheath 34 and a second position in which the outer shaft 16 has been retracted proximally relative to the inner shaft 18, thereby deploying the implant assembly 20 out of the distal end region of the delivery sheath 34. The individual components of the implant assembly 20 will be described in greater detail below.

Figure 2:
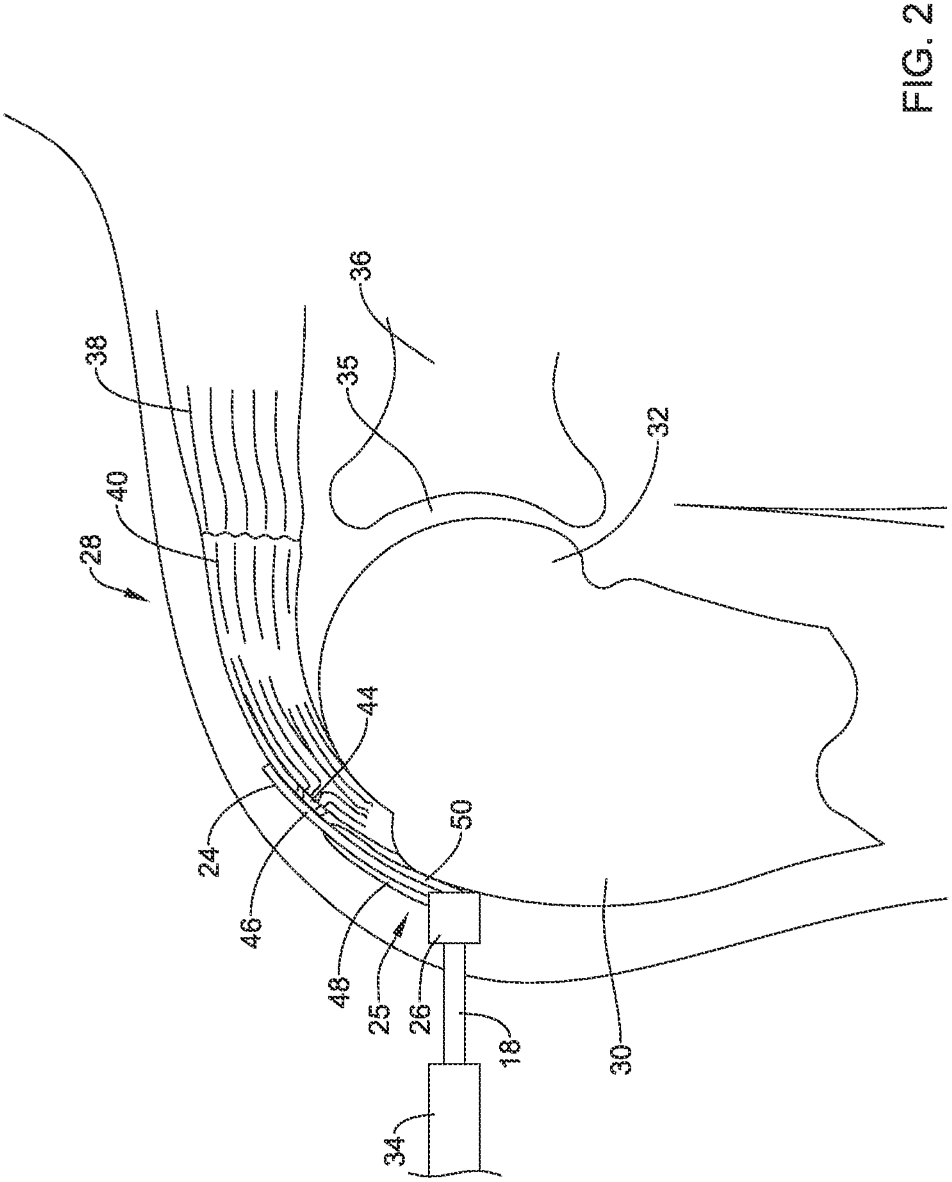
FIG. 2 illustrates a shoulder including a head of the humerus mating with the glenoid fossa of the scapula at a glenohumeral joint and an implant being affixed to a tendon using an implant delivery device.

FIG. 2 shows a cross-sectional view of a shoulder 28. The shoulder 28 shows a head 30 of the humerus 32 mating with a glenoid fossa 35 of the scapula 36. The glenoid fossa 35 comprises a shallow depression in the scapula 36. A supraspinatus tendon 38 is also shown. These muscles (along with others) control the movement of the humerus 32 relative to the scapula 36. Additionally, FIG. 2 illustrates that a distal tendon 40 of the supraspinatus tendon 38 meets the humerus 32 at an insertion point 42.

In FIG. 2, the tendon 38 includes a damaged portion 44 located near the insertion point 42. The damaged portion 44 includes a tear 46 extending partially through the tendon 38. The tear 46 may be referred to as a partial thickness tear. The depicted partial thickness tear 46 is on the bursal side of the tendon, however, the tear may also be on the opposite or articular side of the tendon 38 and/or may include internal tears to the tendon 38 not visible on either surface.

FIG. 2 further illustrates the implant delivery system 10 being utilized to insert the tendon repair implant 24 into the shoulder 28 and place it over the partial thickness tear 46. In the example shown in FIG. 2, the tendon repair implant 24 is placed on the bursal side of the tendon regardless of whether the tear is on the bursal side, articular side or within the tendon. Further, the tendon repair implant 24 may overlay multiple tears.

It can be appreciated from FIG. 2 that delivery of the implant 24 (e.g., a sheet-like implant) to a target site of a patient may require a physician to create an incision in the patient sufficient to access the implant site. After creating the access site, the physician may insert a portion of the implant delivery system 10 through the access site and position the distal end of the implant delivery system 10 adjacent the target implant site. The physician may then manipulate the implant delivery system 10 to deploy the implant delivery device assembly 20 (including the implant 24) out of the delivery sheath 34 adjacent the target implant site.

Figure 3:
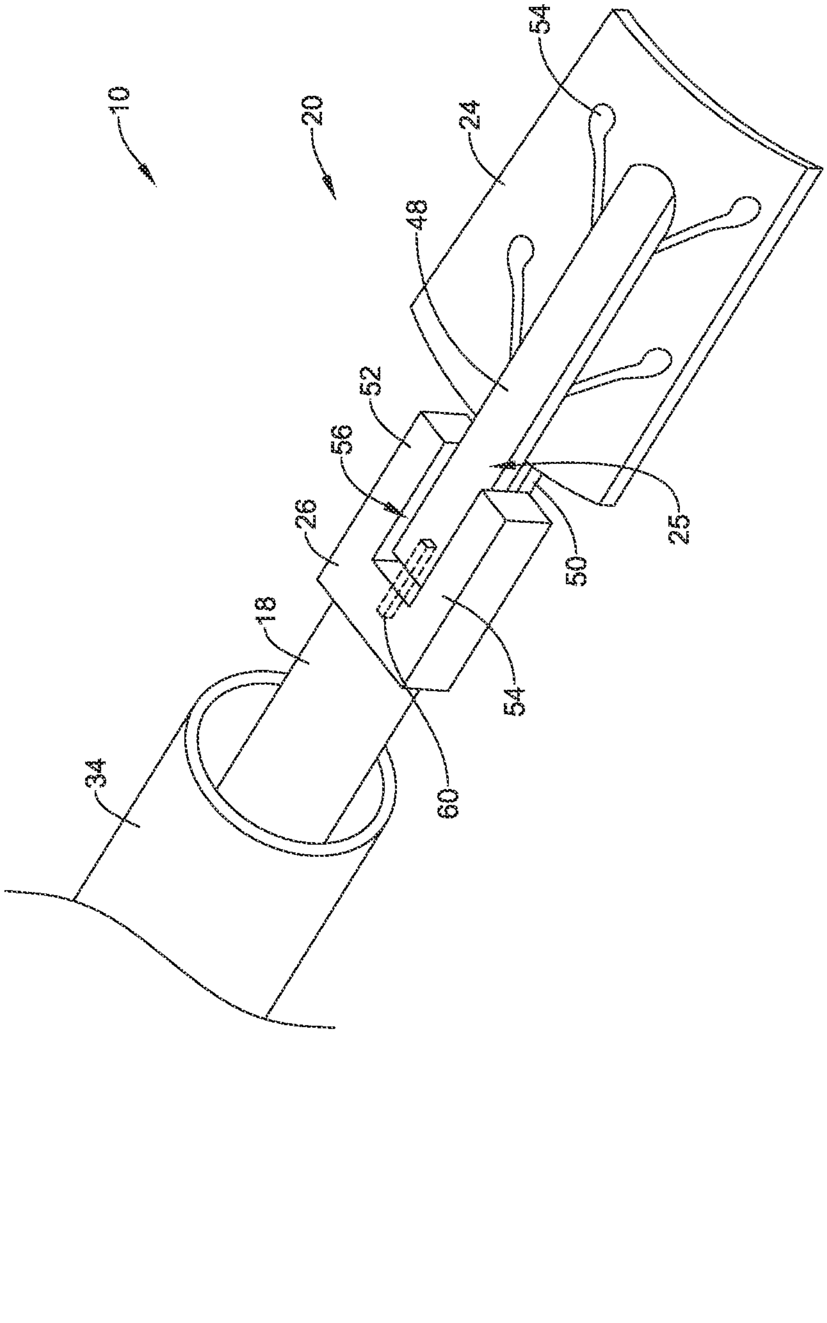
FIG. 3 illustrates an example implant attached to an implant delivery device.

FIG. 3 illustrates that the implant delivery system 10 may include an inner shaft 18 extending within the lumen of the delivery sheath 34 and longitudinally movable relative thereto. The inner shaft 18 may include a proximal end (not shown) extending out of the proximal end of the delivery sheath 34 and/or otherwise manipulatable relative to the delivery sheath 34 by a user. As described above with respect to FIG. 1, the proximal end of the inner shaft 18 and/or the outer shaft 16 may be coupled to a handle 12 (shown in FIG. 1). The handle 12 may be utilized to manipulate the inner shaft 18 relative to the outer shaft 16 and the delivery sheath 34. For example, trigger 14 may be actuated to impart longitudinal movement of the inner shaft 18 relative to the outer shaft 16 and the delivery sheath 34.

Additionally, FIG. 3 illustrates that the distal end of the inner shaft 18 may be coupled to a yoke 26. Additionally, the yoke 26 may be coupled to the implant assembly 20, whereby the implant assembly 20 may include an implant retainer, such as a swivel arm 25, coupled to the implant 24. Further, the swivel arm 25 may include an upper beam 48 and a lower beam 50. It can be appreciated that the swivel arm 25 may be constructed as a monolithic component including an upper beam 48 and a lower beam 50. However, in other instances, the upper beam 48 and the lower beam 50 may be separate components secured together. Further, the upper beam 48 may be aligned longitudinally with the lower beam 50.

Additionally, in some examples, the implant retainer (e.g., the swivel arm 25) may include one or more flexible arms 54. Further, in some examples, the one or more flexible arms 54 may be coupled to the upper beam 48 and/or the implant 24. As will be described in greater detail below, the implant 24 may be secured between the upper beam 48 and the lower beam 50, with the one or more flexible arms 54 positioned along an upper side of the implant 24. In some instances, the one or more flexible arms may be constructed from a shape-memory material (e.g., Nitinol) such that the flexible arms 54 may be flexed, bent, or otherwise deflected for placement within the delivery sheath 34. FIG. 3 further illustrates that the upper beam 48 (which may include the one or more arms 54), the lower beam 50 and the implant 24 may rotate (e.g., pivot, swivel, etc.) with respect to the yoke 26. For example, FIG. 3 illustrates that after the swivel arm 25 (including the upper beam 48, the lower beam 50 and the arms 54) and the implant 24 are deployed out of the distal end of the delivery sheath 34 (via actuation of the trigger 14 of the handle 12), the swivel arm 25 and the implant 24 may pivot relative to the yoke 26 as a user manipulates the placement of the implant 24 along the tendon target site. For instance, the swivel arm 25 and the implant 24 may rotate about a rotational axis extending perpendicular to the longitudinal axis of the inner shaft 18 and/or outer shaft 16. Rotation of the swivel arm 25 and the implant 24 relative to the yoke 26 will be described in greater detail below.

As described above, FIG. 3 illustrates a perspective view of a portion of the implant delivery system 10. FIG. 3 shows the inner shaft 18 extending out of a distal end of the delivery sheath 34. Further, FIG. 3 illustrates the proximal end region of the yoke 26 attached to the distal end of the inner shaft 18. Further yet, FIG. 3 illustrates the swivel arm 25 pivotably coupled to the yoke 26.

In at least some examples, as described above, the implant 24 may be disposed between the upper beam 48 and the lower beam 50, whereby the upper beam 48 and the lower beam 50 may releasably retain the implant 24 therebetween. For example, the upper beam 48 and the lower beam 50 may passively retain the implant 24 when the implant 24 is positioned between the upper beam 48 and the lower beam 50, such as by contact forces between the upper beam 48 and the implant 24 and the lower beam 50 and the implant 24. However, in other examples, the implant 24 may include one or more features which help retain the implant 24 between the upper beam 48 and the lower beam 50.

Additionally, as described above, when the implant 24 is disposed between the upper beam 48 and the lower beam 50, the implant 24 may be positioned such that the one or more arms 54 engage the upper face of the implant 24 along with the upper beam 48. It can be appreciated that the arms 54 may aid in unfolding, unwrapping, flattening, or otherwise manipulating the positioning of the implant 24 at a target site.

FIG. 3 illustrates the flexible arms 54 in a deployed configuration. It can be appreciated that in a deployed configuration, the arms 54 may include four flat heads positioned at a distal end region of each of the four arms, respectively, whereby each of the four arms extend at an angle from the upper beam 48. It can be further appreciated that, in some examples, the arms 54 may be separate components that are fixedly attached to the upper beam 48. However, in other examples, the flexible arms 54 may be formed as a monolithic component with the upper beam 48.

Additionally, as described above, it can be appreciated that the arms 54 may be designed to fit within the lumen of the delivery sheath 34 when being advanced to a target site. Accordingly, it can be further appreciated that, when positioned within the lumen of the delivery sheath 34, each arm 54 may elastically deform, fold, deflect, bend, flex, etc. in a manner to allow for insertion of implant device 24 into the lumen of the delivery sheath 34. Accordingly, the arms 54 may generally be flexible, whereby each arm 54 may bend, twist, fold, wrap or otherwise deform in order for implant 24 to fit within the delivery sheath 34 and then revert to an expanded state (shown in FIG. 3) when unconstrained by the delivery sheath 34.

Figure 6:
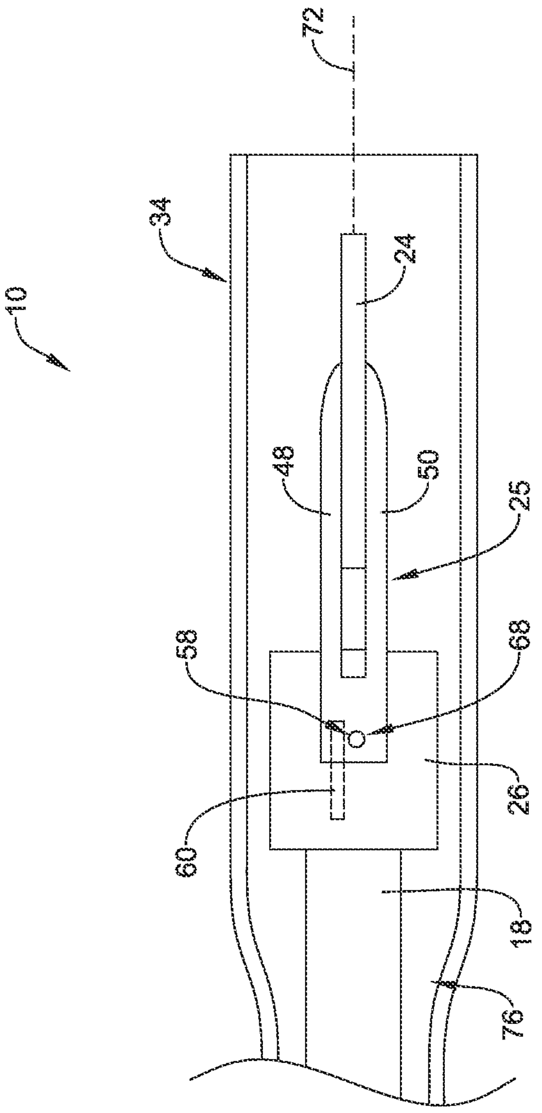
FIG. 6 illustrates an example implant delivery device in a first position.
Figure 7:
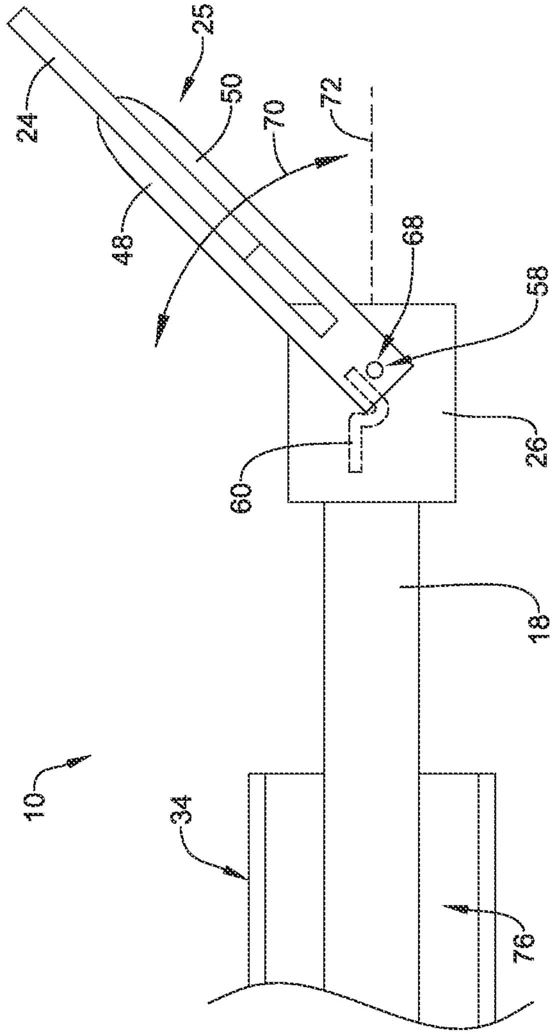
FIG. 7 illustrates the implant delivery device of FIG. 6 in a second position.

FIG. 3 further illustrates the swivel arm 25 (which may include the upper beam 48 and the lower beam 50) coupled to the yoke 26. In some examples, the yoke 26 may generally include a "U-shaped" component defined by a first longitudinal arm 52 and a second longitudinal arm 53. As illustrated in FIG. 3, the first longitudinal arm 52 may be spaced away from the second longitudinal arm 53 to define an opening 56 (e.g., slot) within which a proximal portion of the swivel arm 25 may be positioned. It can be appreciated that the opening 56 may permit the swivel arm 25 (including the upper beam 48 and the lower beam 50) to rotate relative to the longitudinal axis of the yoke 26. For reference, FIG. 6 illustrates a configuration in which the upper beam 48 and the lower beam 50 are aligned substantially parallel to the longitudinal axis of the yoke 26, and thus substantially parallel to the longitudinal axis of the inner shaft 18. Further, FIG. 7 illustrates the rotation of the upper beam 48 and the lower beam 50 about a rotational axis perpendicular to the longitudinal axis of the yoke 26 and the inner shaft 18 such that the swivel arm 25 is angled away from the longitudinal axis of the yoke 26. In some embodiments the swivel arm 5 may be permitted to rotate to an angle of 45 degrees or more, 60 degrees or more 80 degrees or more, or 90 degrees or more away from the longitudinal axis of the yoke 26 and the inner shaft 18.

FIG. 3 further illustrates that the implant delivery system 10 may include a spring component 60 configured to position the swivel arm 25 at a desired equilibrium position or non-deflected position, yet allow the swivel arm 25 to pivot or rotate away from the equilibrium position when subjected to an external force. For example the spring component 60 may be coupled between the yoke 26 and the swivel arm 25, for example extending from a proximal portion of the yoke 26 into a proximal region of the swivel arm 25. As will be described in greater detail below, the spring component 60 may be designed to elastically flex from a first configuration in which it is substantially parallel to the longitudinal axis of the yoke 26, to a second configuration in which it curves away from the longitudinal axis of the yoke 26. The spring component 60 and its configuration relative to the yoke 26 and the swivel arm 25 will be described in greater detail below.

Figure 4:
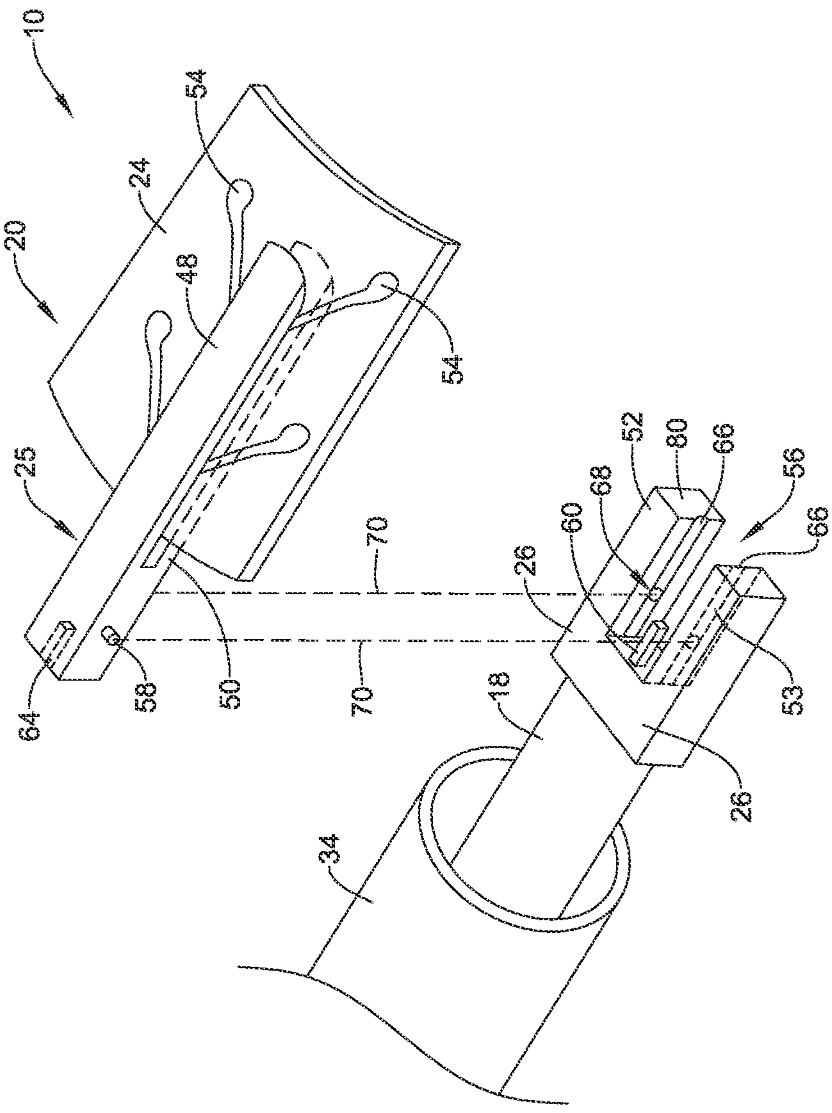
FIG. 4 illustrates an exploded view of a portion of the implant delivery device shown in FIG. 3.

FIG. 4 is a partially exploded view of the implant delivery system 10 described in FIG. 3. Specifically, FIG. 4 illustrates the implant assembly 20 (including the swivel arm 25 and the implant 24) removed from the yoke 26. As discussed above, FIG. 4 illustrates that the upper beam 48 may be vertically aligned with the lower beam 50, whereby the implant 24 is sandwiched between the upper beam 48 and the lower beam 50. Further, FIG. 4 illustrates that, in some examples, the proximal end region of the swivel arm 25 may include one or more projections 58 extending away from the lateral faces (e.g., the left and right sides) of the swivel arm 25. The projections 58 may be substantially cylindrical in shape, however, other shapes are contemplated. For example, the projections may be rounded, ovular, triangular, pointed, or the like. In other examples, the projections may be semi-spherical in shape and resemble rounded bumps extending away from the lateral faces of the swivel arm 25.

FIG. 4 further illustrates that the proximal end region of the swivel arm 25 may further include a longitudinally extending bore positioned therein. It can be appreciated that the longitudinally extending bore 64 may be designed to accept the spring component 60 (shown extending out of the proximal end region of the yoke 26 in FIG. 4). While the spring component 60 and the bore 64 are illustrated as generally including a rectangular shape in FIG. 4, other configurations are contemplated. For example, it is contemplated that the spring component 60 may be shaped as a flat ribbon, a cylinder, a spiral, a coil, a zig-zag, a tube, or the like. Further, the spring component 60 may include one or more undulations, waves, etc. It can be further appreciated that for any given shape and/or configuration the spring component 60 includes, the bore 63 may include a mating shape which accepts the particular shape of the spring component 60. In other embodiments, the spring component 60 may be secured to and extend proximally from the swivel arm 25 into a bore formed in the yoke 26.

FIG. 4 further illustrates that the yoke 26 may further include one or more longitudinal channels 66, each of which are positioned along an interior surface of the yoke 26 (e.g., an interior surface of each of the first longitudinal arm 52 and the second longitudinal arm 53) and extend proximally from the distally facing front face 80 of the yoke 26. Additionally, FIG. 4 illustrates that each channel 66 may be positioned vertically between the top surface and the bottom surface of the yoke 26. For example, in some instances, each channel 66 may be located approximately halfway between the top surface and the bottom surface of the yoke 26.

Additionally, FIG. 4 illustrates that the yoke 26 may include one or more recesses 68 which are designed to mate with the one or more projections 58 of the swivel arm 25. As illustrated in FIG. 4, the one or more recesses 68 may be positioned along each of the longitudinal channels 66 extending along the interior surface of the yoke 26. Additionally, each of the dashed lines 70 illustrates that each of the projections 58 on the swivel arm 25 may be configured to be aligned and inserted into each of the recesses 68 positioned along the interior surface of the yoke 26, respectively.

It can be further appreciated from FIG. 4 that the swivel arm 25 may be coupled to the yoke 26 by aligning, inserting and sliding each of the projections 58 into each of the longitudinal channels 66 extending from the front face 80 of the yoke 26. For example, each of the projections 58 may be aligned with its respective longitudinal channel 66, whereby the swivel arm 25 may then be slid in a distal-to-proximal direction such that each of the projections 58 may be inserted into its respective recess 68. It can be appreciated that the projections 58 may be designed to be press-fit into the recesses 68 such that the swivel arm 25 may be prevented from being separated from the yoke 26, yet still may be free to pivot relative to the yoke 26 about a rotational axis extending through the projections 58.

It can be appreciated that while FIG. 4 illustrates that while the projections 58 may be designed to be inserted into the recesses 68 positioned along the yoke 26, it is also contemplated that, in other examples, the swivel arm 25 may include one or more recesses designed to accept one or more projections extending from the inner surfaces of the yoke 26. In other words, in some examples, the yoke 26 may include one more projections which may be located where the recesses 68 are illustrated in FIG. 4, while the swivel arm 25 may include one or more mating recesses located where the projections 58 are illustrated in FIG. 4. This alternative arrangement would still provide a press-fit arrangement between the projections and the recesses such that the swivel arm 25 may be prevented from being separated from the yoke 26, yet still may be free to pivot relative to the yoke 26 about a rotational axis extending through the projections.

Additionally, while FIG. 4 illustrates that the implant delivery system 10 may include longitudinal channels 66 extending from the front face 80 of the yoke 26, it is also contemplated that the implant delivery system 10 may include one or more vertical channels extending from the upper or lower surface of the yoke 26. In these examples, the projections 58 of the swivel arm 25 may be free to translate vertically within the vertical channels. In other words, the "pivot point" of the swivel arm (e.g., the rotational axis which may correspond and extend through the projections 58) may be free to move vertically up or down (toward the upper of lower surface) of the yoke 26 as the swivel arm 25 rotates relative to the yoke 26.

Additionally, while FIG. 4 illustrates that spring component 60 may be fixedly attached to the yoke 26 and extend into a bore 64 located in the proximal end region of the swivel arm 25, it is contemplated that, in other examples, the spring component 60 may be fixedly attached to the proximal end region of the swivel arm 25 and extend into a bore located in the yoke 26. This arrangement would still permit the spring component 60 to shift between a first configuration in which it is substantially parallel to the longitudinal axis of the yoke 26 and a second configuration in which it flexes relative to the longitudinal axis of the yoke 26.

Figure 5:
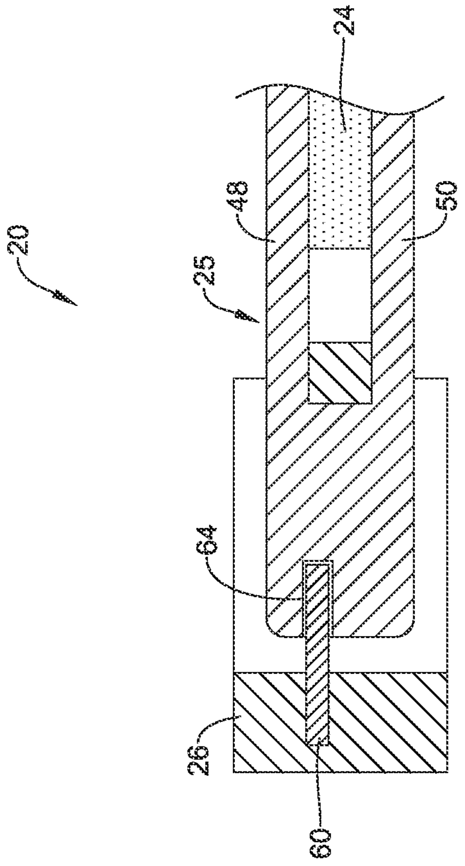
FIG. 5 illustrates a cross-sectional view taken along line 5-5 of FIG. 3.

FIG. 5 illustrates a cross-sectional view of the implant positioning assembly 20 taken along line 5-5 of FIG. 3. FIG. 5 illustrates the implant 24 being positioned between the upper beam 48 and the lower beam 50 of the swivel arm 25. Further, FIG. 5 illustrates the proximal end region of the swivel arm 25 positioned within the opening 56 shown in FIGS. 3-4) of the yoke 26. Additionally, FIG. 5 shows the spring component 60 fixedly attached to the proximal end portion of the yoke 26 and extending into the bore 64 located in the proximal end region of the swivel arm 25.

FIG. 6 illustrates the implant delivery system 10 including the inner shaft 18, the yoke 26, the swivel arm 25 and the implant 24 positioned within the lumen 76 of the delivery sheath 34. As discussed above, the swivel arm 25 may include the upper beam 48 and the lower beam 50 between which the implant 24 is positioned (it is noted that, for simplicity purposes, the flexible fingers 54 are not shown in FIGS. 6-9). FIG. 6 further illustrates the projection 58 of the swivel arm 25 positioned within the recess 68 of the yoke 26. Additionally, FIG. 6 illustrates the spring component 60 fixedly attached to the proximal end portion of the yoke 26 and extending into the bore 64 (shown in FIG. 5) located in the proximal end region of the swivel arm 25. It can be appreciated that when positioned within the lumen 76 of the delivery sheath 34 (e.g., in a delivery configuration prior to being deployed from the delivery sheath 34), the swivel arm 25 (including the upper beam 48 and the lower beam 50) and the implant 24 may be aligned substantially parallel to the longitudinal axis 72 of the delivery sheath 34.

FIG. 7 illustrates the implant delivery system 10 shown in FIG. 6 after the outer shaft 16 has been retracted in a distal-to-proximal direction. As discussed above, actuation of the trigger 14 of the handle 12 (shown in FIG. 1) may retract the outer shaft 16 and delivery sheath 34 relative to the inner shaft 18, yoke 26, swivel arm 25 (including the upper beam 48 and the lower beam 50) and the implant 24. Accordingly, FIG. 7 illustrates that the proximal retraction of the outer shaft 16 may deploy the yoke 26, the swivel arm 25 (including the upper beam 48 and the lower beam 50) and the implant 24 out of the delivery sheath 34.

FIG. 7 further illustrates that after being deployed out of the delivery sheath 34, the swivel arm 25 may rotate relative to the yoke 26. For example, FIG. 7 illustrates the swivel arm 25 (including the upper beam 48 and the lower beam 50) may rotate away from the longitudinal axis 72 (rotation of the swivel arm 25 is depicted by the curved arrow 70 in FIG. 7). As described above, it can be appreciated that the swivel arm 25 may pivot about the recess 68 of the yoke 26.

It can be further appreciated that, in some examples, the spring component 60 may bias the swivel arm 25 to rotate from the position shown in FIG. 6 (whereby the swivel arm 25 is aligned with the longitudinal axis 72) to the position shown in FIG. 7 (whereby the swivel arm 25 is rotated away from the longitudinal axis 72). For example, in some examples, the spring component 60 may be constructed from a shape-memory material (e.g., a nickel-titanium alloy) which allows it to flex or otherwise deform after the outer shaft 16 is retracted, thereby rotating the swivel arm 25 relative to the yoke 26, as described above.

However, in other instances, the spring component 60 may be designed such that it biases the swivel arm 25 to be aligned with the longitudinal axis 72, yet still permits the swivel arm 25 to rotate relative to the yoke 26. Referring back to FIG. 2, for example, the implant delivery system 10 may be designed such that the swivel arm 25 may initially be deployed out of the delivery sheath 34 in a substantially straight configuration, whereby the swivel arm 25 may then rotate with respect to the yoke 26 from an applied external force as the swivel arm 25 (and implant 24) are positioned closer to the tendon target site.

Figure 8:
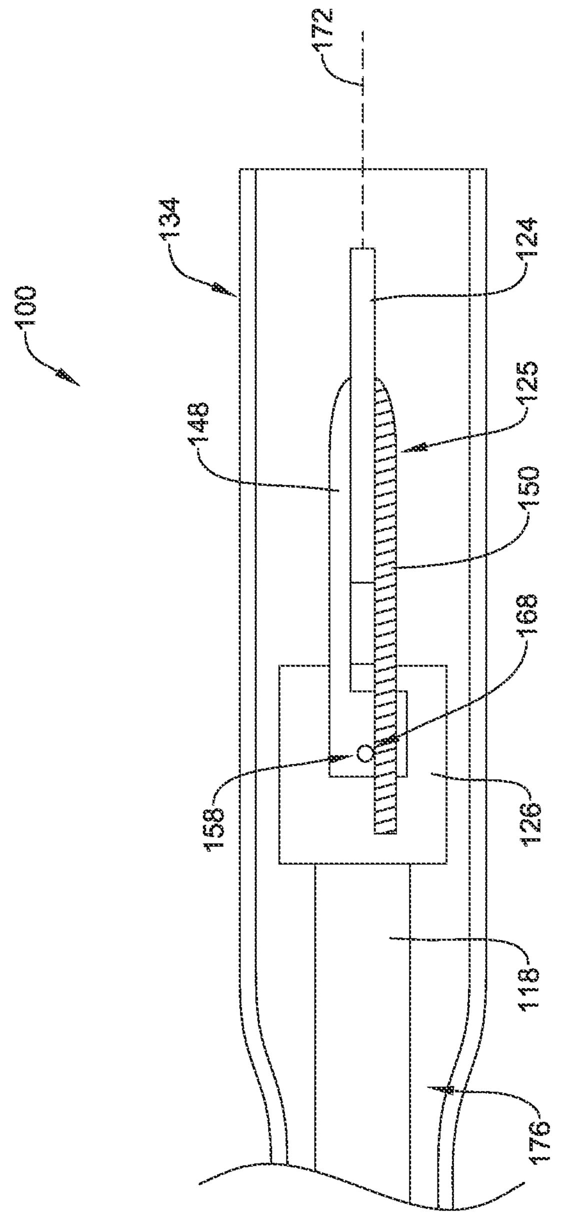
FIG. 8 illustrates another implant delivery device in a first position.

FIG. 8 illustrates a portion of another example implant delivery system 100. The portion of the implant delivery system 100 shown in FIG. 8 may be similar in form and function to the implant delivery system 10 described above. For example, the implant delivery system 100 may include an inner shaft 118 extending within the lumen 176 of the delivery sheath 134. Further, the distal end of the inner shaft 118 may be coupled to a yoke 126. Additionally, a swivel arm 125 may be pivotably coupled to the yoke 126. The swivel arm 125 may include an upper beam 148 and a lower beam 150. Further, an implant 124 may be positioned between the upper beam 148 and the lower beam 150 with the upper beam 148 and the lower beam 150 applying a compressive force on the implant 124 to securely hold the implant 124 therebetween. The swivel arm 125 may further include one or more projections 158 which engage one or more recesses on the yoke 126, thereby permitting the upper beam 148 and the lower beam 150 to rotate relative to the yoke 126 about a rotational axis extending through the projections 158 and perpendicular to the longitudinal axis of the inner shaft 118 and yoke 126.

FIG. 8 further illustrates that, in some examples, the lower beam 150 may be formed from a material which is similar in form and function to the material utilized to construct the spring component 60 in the implant delivery system 10 described above. For example, the lower beam 150 may be formed from an elastic material (e.g., a flexible metal material) designed to flex or deflect between a first position (e.g., a position in which the swivel arm 125 is aligned with the longitudinal axis 172) to a second position shown in FIG. 9 (e.g., a position in which the swivel arm 125 is rotated away from the longitudinal axis 172). In some examples, the lower beam 150 may be constructed from a shape-memory material (e.g., a nickel-titanium alloy).

Figure 9:
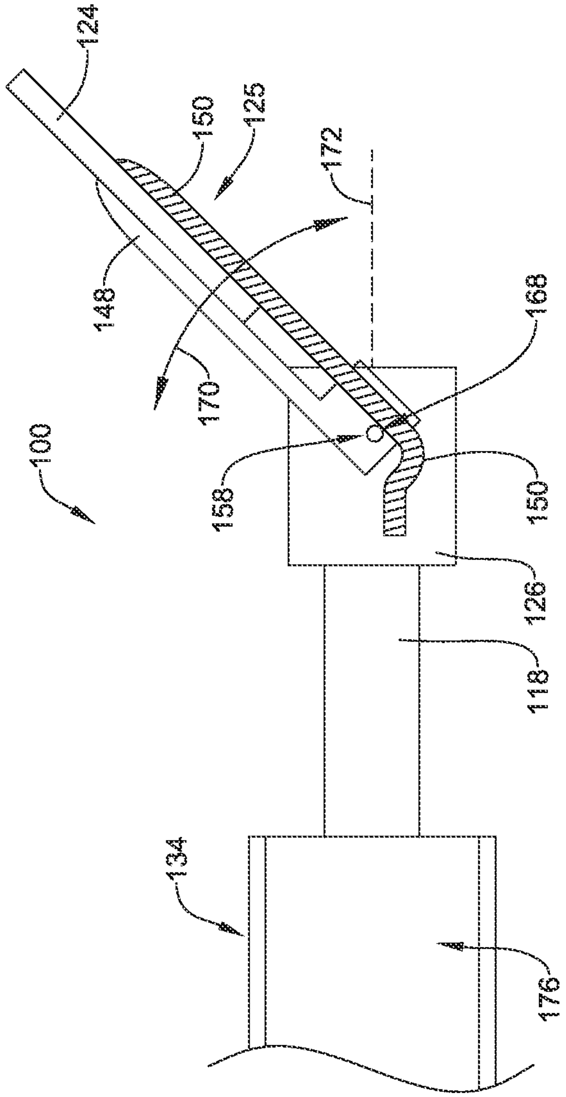
FIG. 9 illustrates the implant delivery device of FIG. 8 in a second position.

In some examples, the lower beam 150 may be constructed from a shape-memory material which biases the swivel arm 25 to rotate from the axially aligned position shown in FIG. 8 (whereby the swivel arm 125 is aligned with the longitudinal axis 172 of the delivery sheath 134) to the angled position shown in FIG. 9 (whereby the lower beam 150 bends and rotates the swivel arm 125 away from the longitudinal axis 172 of the delivery sheath 134 to position the swivel arm 25 at an oblique or perpendicular angle to the longitudinal axis 172). In some examples, the lower beam 150 may be constructed from a shape-memory material (e.g., a nickel-titanium alloy) which allows it to bend or otherwise deform after the delivery sheath 134 is retracted, thereby rotating the swivel arm 125 relative to the yoke 126 as described above.

However, in other instances, the lower beam 150 may be designed such that it biases the swivel arm 125 to be aligned with the longitudinal axis 172, yet still permits the swivel arm 125 to rotate relative to the yoke 126 when subjected to an applied external force. Referring back to FIG. 2, for example, the implant delivery system 100 may be designed such that the swivel arm 125 may be initially deployed out of the delivery sheath 134 in a substantially straight configuration, whereby the swivel arm 125 may rotate with respect to the yoke 126 from an applied external force as the swivel arm 125 (and the implant 124) are positioned closer to the tendon target site.

It can be appreciated that the lower beam 150 may be attached to the upper beam 148 using a variety of attachment techniques. In some instances, the lower beam 150 may be fixedly attached to the upper beam 148 using an adhesive, screws, pins, tongue and groove techniques, or the like. In other examples, such as the example shown in FIG. 8, the lower beam 150 may be inserted through an aperture (e.g., a bore) extending within the upper beam 148. It can be appreciated the portion of the lower beam 150 extending within the aperture of the upper beam 148 may be fixedly attached to the upper beam 148 (via and adhesive, for example). In other instances, the lower beam 150 may be slidably coupled to the upper beam by passing the lower beam 150 through the aperture of the upper beam 148.

Figure 10:
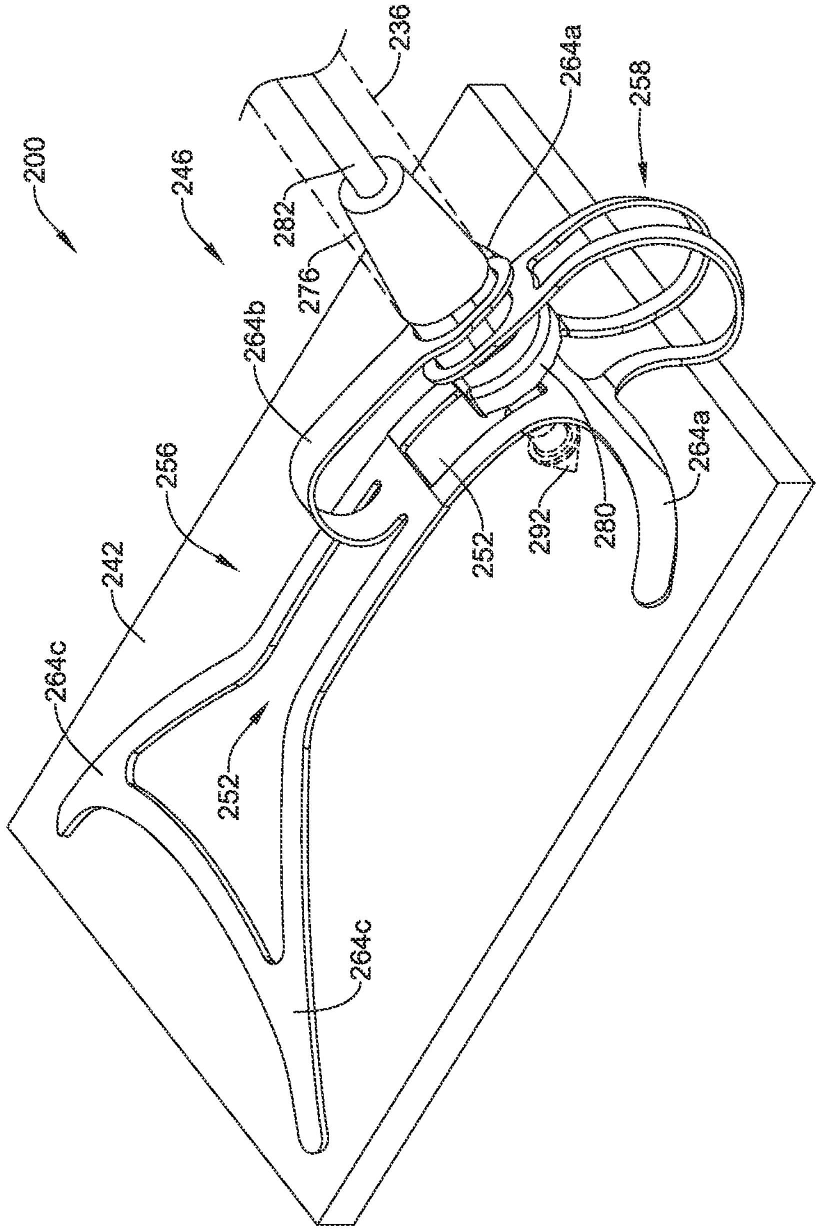
FIG. 10 illustrates another implant delivery device attached to an example implant delivery system.
Figure 11:
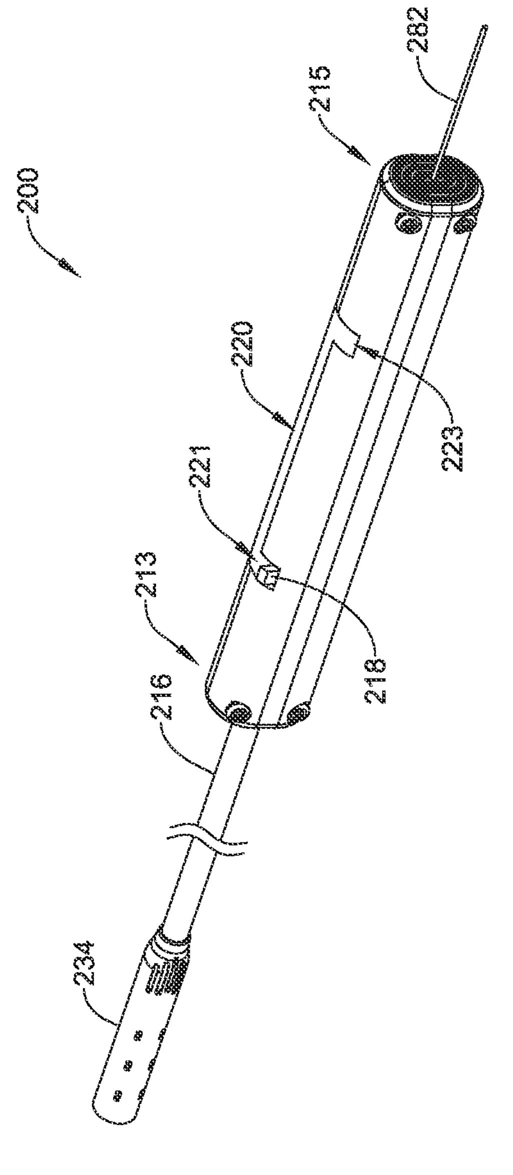
FIG. 11 is a perspective view of another implant delivery system.

FIG. 10 illustrates a portion of another implant delivery system 200 (the full implant delivery system 200 is shown in FIG. 11) including an implant 224 coupled to an example frame 246 (e.g., implant deployment device, implant retainer). Various components of the implant delivery system 200 may be similar in form and function with the implant delivery system 10 described above. For example, as shown in FIG. 11, the implant delivery system 200 may include an outer shaft 216 coupled to a handle 212. Further, like the outer shaft 16 and delivery sheath 34 described herein, the distal end of the outer shaft 216 may include a delivery sheath 234. The frame 246 may be positioned within the lumen of the delivery sheath 234 while being advanced to a target site. Further, it can be appreciated that actuation of an actuation member 218 coupled to the handle 212 may retract the outer shaft 216, thereby deploying the frame 246 and implant 224 out of the delivery sheath 234.

Like that described above with respect to the implant delivery system 10, delivery of the implant delivery system 200 may include the insertion of the outer shaft 216 and delivery sheath 234 through an access site (e.g., incision) and advancement to a target site. During advancement to the target site, the detachable frame 246 and the implant 224 (in combination) may be wrapped and/or folded upon itself such that they are positioned within the lumen of the delivery sheath 234. Further, the combination of the detachable frame 246 and the implant 224 may remain wrapped and/or folded within the lumen of the delivery sheath 234 until deployed from the delivery sheath 234.

For example, after positioning the distal end of the delivery sheath 234 proximate the target site, a clinician may deploy the detachable frame 246 (in combination with the implant 224) out of the lumen of the delivery sheath 234, such as by retracting the outer shaft 216 and delivery sheath 234 and positioning the implant 224 and the frame 246 over the target site. As will be described in greater detail below, the frame 246 and the implant 224 may automatically expand to an open state when unconstrained by the delivery sheath 234. Further, in some examples, the frame 246 may be "shape set" such that its deployed configuration may generally match the curvature of the humeral head. In other words, the frame 246 may expand to a substantially curved configuration which matches the curvature of the humeral head when unconstrained by the delivery sheath 234.

As shown in FIG. 10, the detachable frame 246 may include a body portion 256. In some examples, the body portion 256 may resemble a square, rectangular, circular, ovular, or similarly shaped framework from which other members may extend. For example, the body portion 256 of the frame 246 may bear some resemblance to an elongated rectangle having a proximal portion and a distal portion. Further, the body portion 256 may include one or more apertures defined between struts of the body portion 256. Additionally, FIG. 10 illustrates that the frame 246 may further include a connector leg 264 and a head portion 258, which may be utilized to connect the frame 246 to other components (e.g., an inner shaft 236 and a tether 282 shown in FIG. 10) of the implant delivery system 200. It is noted that the inner shaft 236 is depicted in dashed lines and extending over a collar 276, the details of which will be described in greater detail below. Additionally, FIG. 10 further illustrates that the frame 246 may include one or more attachment arms **264*a*/264*c* which may be utilized to releasably attach the implant 224 to the frame 246**.

It can be appreciated that the detachable frame 246 may be a monolithic structure formed of a superelastic metal material, such as nitinol. However, it is also contemplated that the detachable frame 246 may be constructed using alternative materials and/or manufacturing methodologies. For example, the frame 246, or portions thereof, may be constructed from a polymeric material, a ceramic material and/or other various materials. Additionally, the frame 246 may be manufactured via an injection molding or alternative polymer manufacturing methodologies. Alternatively, the frame 246 may be formed through a 3-D printing process, if desired. Further, different portions of the frame 246 (as described above, for example), may be made from a variety of materials and combined using alternative methodologies. For example, the attachment arms **264*a*/264*c* may be made from a polymer material and combined with a central frame member constructed from a metal material. Variations of combining different materials with different portions of the frame 246** are contemplated.

FIG. 10 further illustrates that the implant delivery system 200 described herein may include a tack member 292 designed to secure the delivery system 200 in place prior to a clinician affixing the implant 224 to the bone and/or tendon. For example, FIG. 10 illustrates a tack member 292 extending distally from a tack disk 280. As shown in FIG. 10, the tack member 292 may extend distally from the tack disk 280 and be substantially perpendicular to the implant 224 and/or frame 246.

In some instances, the tack member 292 may resemble a cylindrical pin or rod extending away from the frame 246. Additionally, the tack member 292 may be designed to be rigid enough to be pounded and/or inserted into bone. For example, in some instances, a clinician may apply a force to a proximal portion of the implant delivery system 200 (e.g., on the proximal end of the inner shaft 236) such that the tack member 292 may be "hammered" into a body structure (e.g., bone). As shown in FIG. 10, the tack member 292 may include a tapered distal tip, which may be a sharpened or blunt tapered distal tip in some instances. FIG. 10 illustrates that the tack member 292 may extend through one of the apertures 252 defined in the body portion 256 when the frame 246 is in the deployed configuration of FIG. 10. Furthermore, the tack member 292 may extend through the implant 224 when attached to the frame 246 in the deployed configuration (as shown in FIG. 10).

FIG. 10 further illustrates that the implant delivery system 200 may further include a tether 282 secured to the proximal end of the tack member 292, such as coupled to a tack disk 280, which in turn may be coupled to or formed as a portion of the tack member 292. Therefore, the tack member 292 may be secured to the tether 282 via the tack disk 280. Accordingly, after the tack member 292 has been inserted into bone, retraction of the tether 282 may pull on the tack member 292, thereby releasing it from a target site (e.g., a bone).

Further, the frame 246 may also be coupled to the tether 282 via a connection, such as the combination of the tack disk 280 and a collar 276. It can be appreciated that both the tack disk 280 and the collar 276 may be fixedly attached to the tether 282. Additionally, as discussed above, FIG. 10 illustrates that the tack disk 280 may be coupled to both the head portion 258 and the connector leg **264*b* of the frame 246. In particular, the head portion 258 and the connector leg 264*b* may be "sandwiched" between a distal facing surface or rim of the collar 276 and a proximal facing surface or rim of the tack disk 280. In other words, the head portion 258 and the connector leg 264*b* of the frame 246 may be constrained between the collar 276 and the tack disk 280. Therefore, the frame 246 may be coupled to the tether 282 via being sandwiched between the collar 276 and the tack disk 280**.

As described above, the implant delivery system 200 may include an inner shaft 236 which may extend within the lumen of the outer shaft 216 and be longitudinally movable relative thereto. In some examples, the proximal end of the inner shaft 236 and/or the outer shaft 216 may be coupled to the handle 212. Further, the distal end of the inner shaft 236 may be designed to engage the collar 276. For example, the lumen of the inner shaft 236 may be designed to mate with the outer profile of the collar 276, thereby permitting the distal end of the inner shaft 236 to extend over the collar 276. Accordingly, manipulation of the inner shaft 236 may impart movement to the collar 276 (and consequently, the frame 246). It can be appreciated that the handle 212 may be utilized to manipulate the inner shaft 236 relative to the outer shaft 216 and the delivery sheath 234. For example, the handle 212 may be utilized to impart a rotational force to the inner shaft 236 and/or longitudinal movement of the inner shaft 236 relative to the outer shaft 216 and delivery sheath 234. In some instances, the tether 282 may extend through the lumen of the inner shaft 236 proximally to the handle 220. The frame 246 may be detachable from the inner shaft 236 such that the inner shaft 236, the outer shaft 216 and handle 212 may be removed while the frame 246 may remain attached to the tether 282.

As discussed above, FIG. 11 illustrates the entire example implant delivery system 200. The implant delivery system 200 may include a handle 212. FIG. 11 further illustrates the implant delivery system 200 includes the delivery sheath 234, which my house the combination frame 246 and implant 224 (shown in FIG. 10). FIG. 11 illustrates that the handle 212 may be attached to the delivery sheath 234 via an outer shaft 216.

As discussed above, the delivery sheath 234 may surround the frame 246 and implant 224 when in a delivery configuration. In other words, the frame 246 and implant 224 may be contained in a collapsed, folded delivery configuration within the lumen of the delivery sheath 234 during delivery to a treatment site. For example, it can be appreciated that in a delivery configuration, the implant 224 may be attached to the frame 246, whereby the implant 224 and frame 246 (together) may be folded and positioned within the delivery sheath 234.

Additionally, it can be appreciated that retraction of the outer shaft 216 may release (e.g., deploy) the implant 224 and frame 246 from the delivery sheath 234. In other words, the implant 224 and frame 246 may be positioned within the delivery sheath 234 as the outer shaft 216 is inserted into a patient's body and advanced toward a target site. After being positioned at the target site, the outer shaft 216, and delivery sheath 234 secured thereto, may be retracted while the inner shaft 236 may be held stationary relative to the outer shaft 216. As discussed above, retraction of the outer shaft 216 relative to the inner shaft 236 and frame 246 may retract the delivery sheath 234 relative thereto, which uncovers (e.g., releases) and deploys the implant 224 and the frame 246.

FIG. 11 further illustrates that the handle 212 may include an actuation member 218 (e.g., trigger) positioned within a first circumferential recess 221 of a channel 220. As will be described in greater detail below, actuation of the actuation member 218 (via translating the actuation member 218 within the channel 220) may retract the outer shaft 216 relative to the inner shaft 236 and handle 212. Additionally, it can be appreciated that the actuation member 218 may be fixedly secured to a proximal end of the outer shaft 216 (while a proximal end of the inner shaft 236 may be fixedly secured to the housing of the handle 212). Accordingly, shifting the actuation member 218 from a position in which it is closer to the distal end 213 of the handle 212 to a position in which it is closer to the proximal end 215 of the handle 212 may retract the outer shaft 216 relative to the inner shaft 236, which may also retract the delivery sheath 234, thereby deploying the frame 246 and implant 224.

FIG. 11 further illustrates the tether 282 extending out of the proximal end 215 of the handle 212. It can be appreciated that to utilize the tether 282 to release the tack member 292, the tether 282 should be accessible to the user. FIG. 11 illustrates the tether 282 extending from the tack member 292, through the inner shaft 236 (which is positioned within the lumen of the outer shaft 216), through the handle 212 to a position outside the handle 212 (e.g., through the handle 212 to a location proximal of the handle 212). As discussed above, the tether 282 may also be secured to the frame 246, such as via the combination of the collar 276 and tack disk 280, or otherwise secured to the frame 246, as described above.

FIG. 11 illustrates the actuation member 218 positioned within the recess 221 of the channel 220. It can be appreciated that when positioned within the recess 221, the actuation member 218 is prevented from shifting in a distal-to-proximal direction, thereby preventing an inadvertent deployment of the frame 246 and implant 224. In other words, until a user chooses to rotate the actuation member 218 out of the recess 221 and slide the actuation member in a distal-to-proximal direction within the longitudinal channel 220, the frame 246 and implant 224 will not deploy. This may be an important safety feature during operation of the implant delivery system 200.

As described above, the tether 282 may be utilized to release the tack member 292 after the tack member 292 has been inserted into bone. It can be appreciated that pulling on the tether 282 requires the tether 282 to move freely relative to the handle 212. However, in some instances, it may be desirable to clamp and secure the tether 282 relative to the handle 212 until a user opts to release it. Accordingly, in some examples, the delivery system 200 may include a tether clamp mechanism 228 (shown in FIG. 13) which may clamp and secure the tether member 282 relative to the handle 212. In some instances, further manipulation of the actuation member 218 after retracting the outer sheath 234 to expose the frame 246 and implant 224 may release or unclamp the tether member 282 from the handle 212. For example, further manipulation of the actuation member 218 may cause the actuation member 218 to move the tether clamp mechanism 228 from a locked or engaged position to an unlocked of disengaged position to release the tether member 282. In some instances, the actuation member 218 may be withdrawn proximally in a longitudinal direction (along the longitudinal axis) to retract the outer sheath 234, and thereafter, further manipulation of the actuation member 218 in a circumferential direction (e.g., rotated about the longitudinal axis) may cause the actuation member 218 to move the tether clamp mechanism 228 from a locked or engaged position to an unlocked of disengaged position to release the tether member 282. One possible configuration is further shown in FIGS. 12-18.

Figure 12:
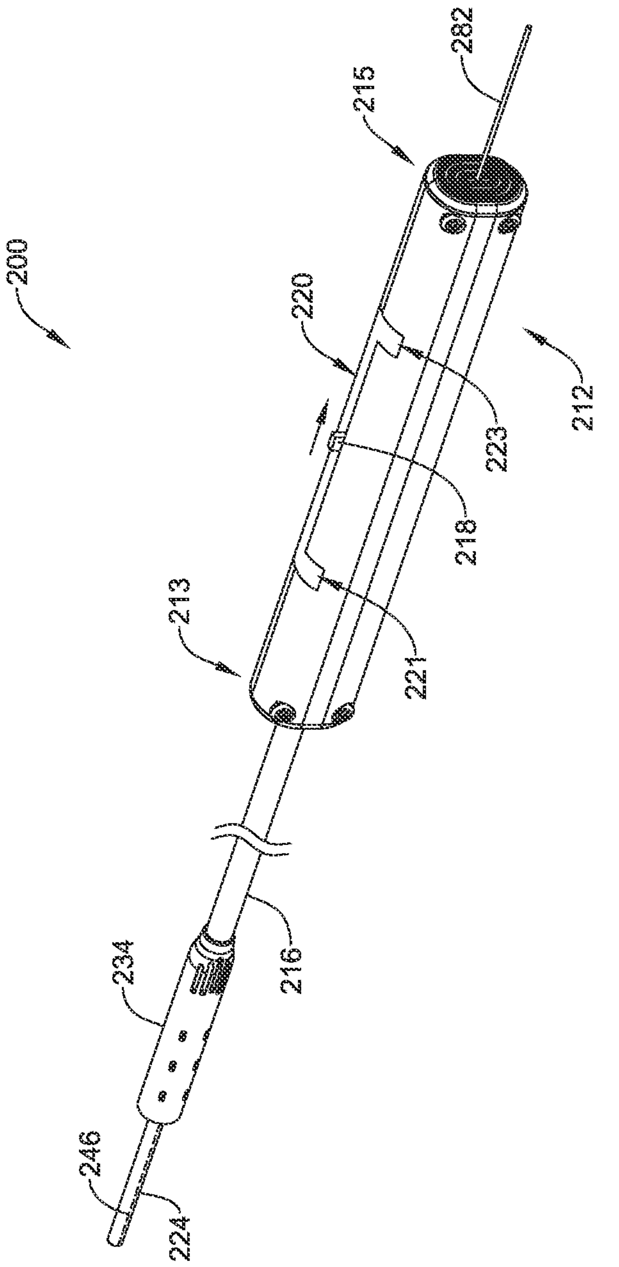
FIG. 12 is another perspective view of the example implant delivery system shown in FIG. 11.

As described above, FIG. 12 illustrates the actuation member 218 has been rotated out of the recess 221 and has been translated in a proximal direction along the longitudinal channel 220 to a position in which it is approximately midway between the first recess 221 and the second recess 223. Further, in the position illustrated in FIG. 12, it can be appreciated that the outer shaft 216 has been retracted such that the implant 224 and frame 246 have been partially deployed out of the lumen of the delivery sheath 234. FIG. 12 shows the implant 224 and frame 246 in a wrapped configuration prior to being fully expanded.

Figure 13:
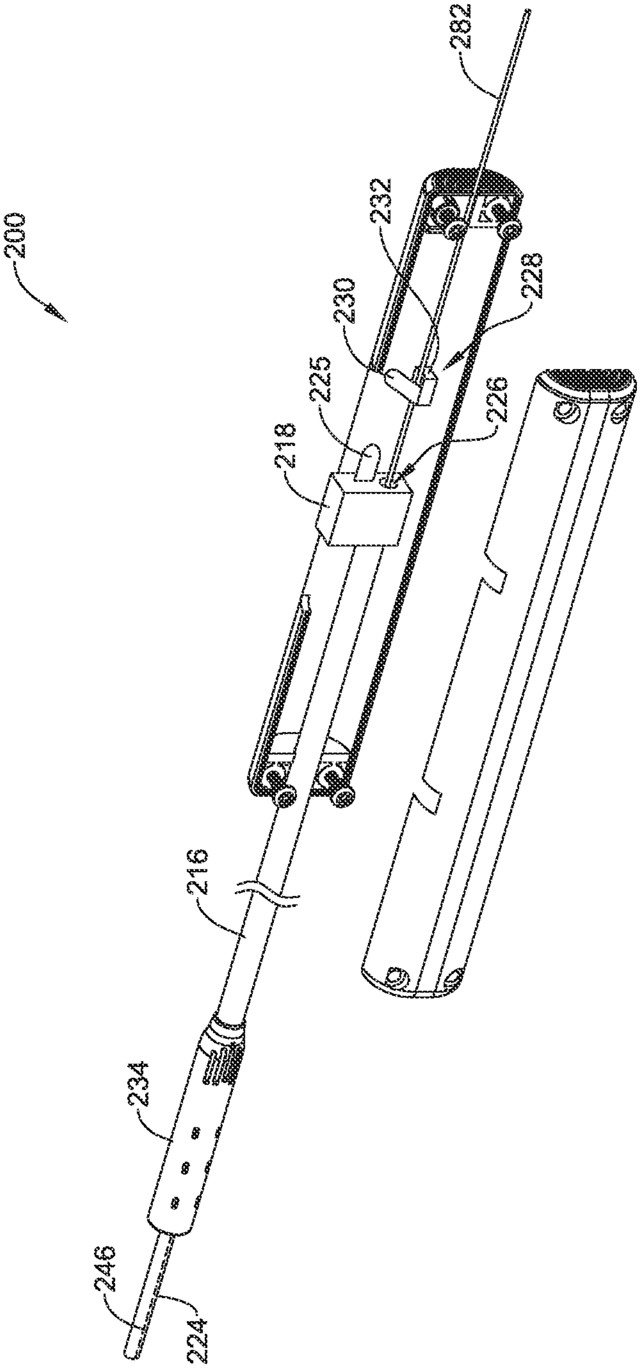
FIG. 13 is an exploded view of the example implant delivery system shown in FIG. 12.

FIG. 13 illustrates a partially exploded view of the handle 212 shown in FIG. 12. As described above, the actuation member 218 has been rotated out of the recess 221 and has been translated in a proximal direction along the channel 220 to a position in which it is approximately midway between the first recess 221 and the second recess 223. FIG. 13 further illustrates the outer shaft 216 extending proximally from the delivery sheath 234 to the actuation member 218. As discussed above, FIG. 13 further illustrates the tether 282 may extend from the tack member 292 (discussed above), through the lumen of the inner shaft 236 (extending through the outer shaft 216), through an aperture 226 located in the actuation member 218, through the tether clamp mechanism 228 and thereafter exit the proximal end of the handle 212.

As discussed above, it can be appreciated that the tether clamp mechanism 228 may fixedly secure the tether 282 from relative longitudinal movement relative to the inner shaft 236, the outer shaft 216 and the handle 212 when in a locked position. FIG. 13 illustrates that the tether clamp mechanism 228 may include a rotatable lever 230 positioned adjacent to a block component 232. As will be described in greater detail below, the tether 282 may extend though the aperture 226 of the actuation member 218 and be juxtaposed along a surface of the block component 232, such as rest along a v-shaped notch of the block component 232 before exiting the proximal end of the handle 212.

Further, the lever 230 may be biased in a first position in which it pinches (e.g., locks, grips, holds, secures) the tether 282 against the surface of the block component 232 (e.g., within the v-shaped notch of the block component 232). For example, the lever 230 may be coupled to a spring (or similar mechanism) which biases the lever 230 to a first position in which it pinches (e.g., locks, grips, holds, secures) the tether 282 against the surface of the block component 232 (e.g., within the v-shaped notch of the block component 232). In other instances, the lever 230 may be flexible and be deflected which biases the lever 230 to a first position in which it pinches (e.g., locks, grips, holds, secures) the tether 282 against the surface of the block component 232 (e.g., within the v-shaped notch of the block component 232) Accordingly, and as will be described in further detail below, the lever 230 may be rotated or otherwise moved away from the block component 232 to free the tether 282. Rotation of the lever 230 may be accomplished using the actuation member 218, as described below.

Figure 14:
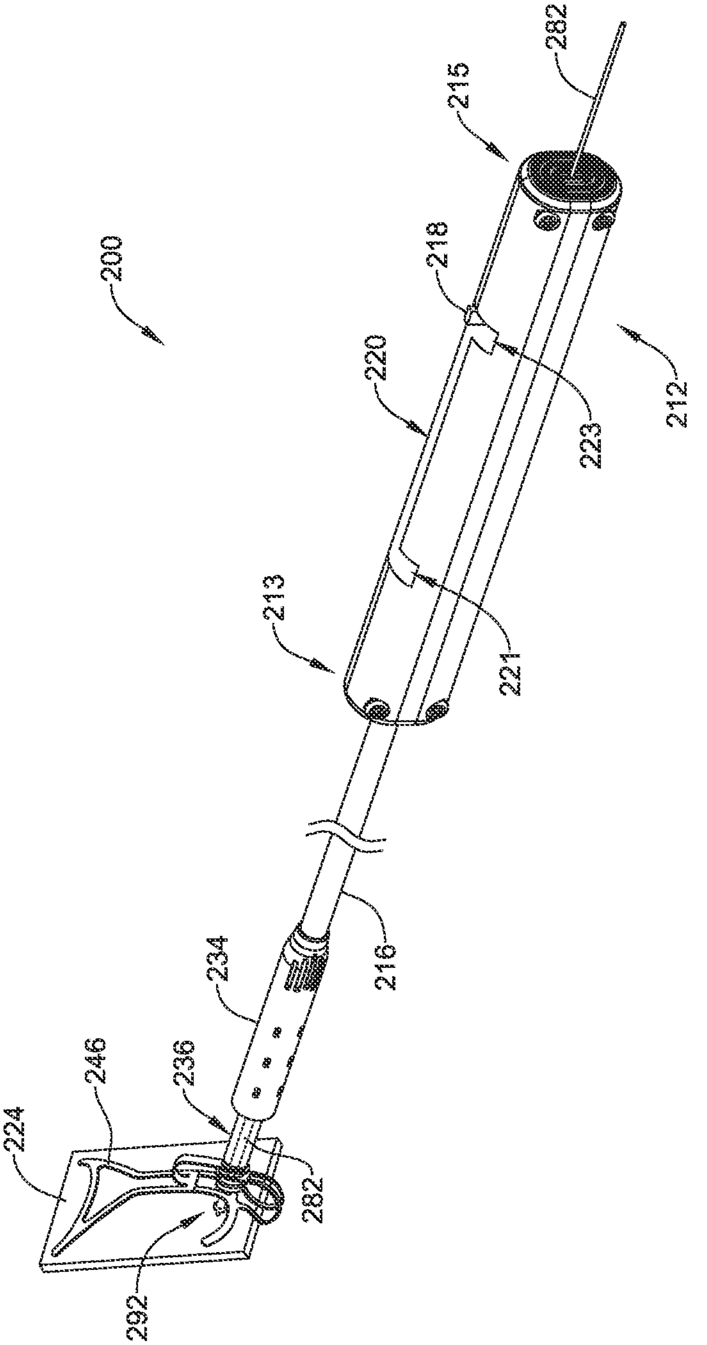
FIG. 14 is another perspective view of the example implant delivery system shown in FIG. 11.
Figure 15:
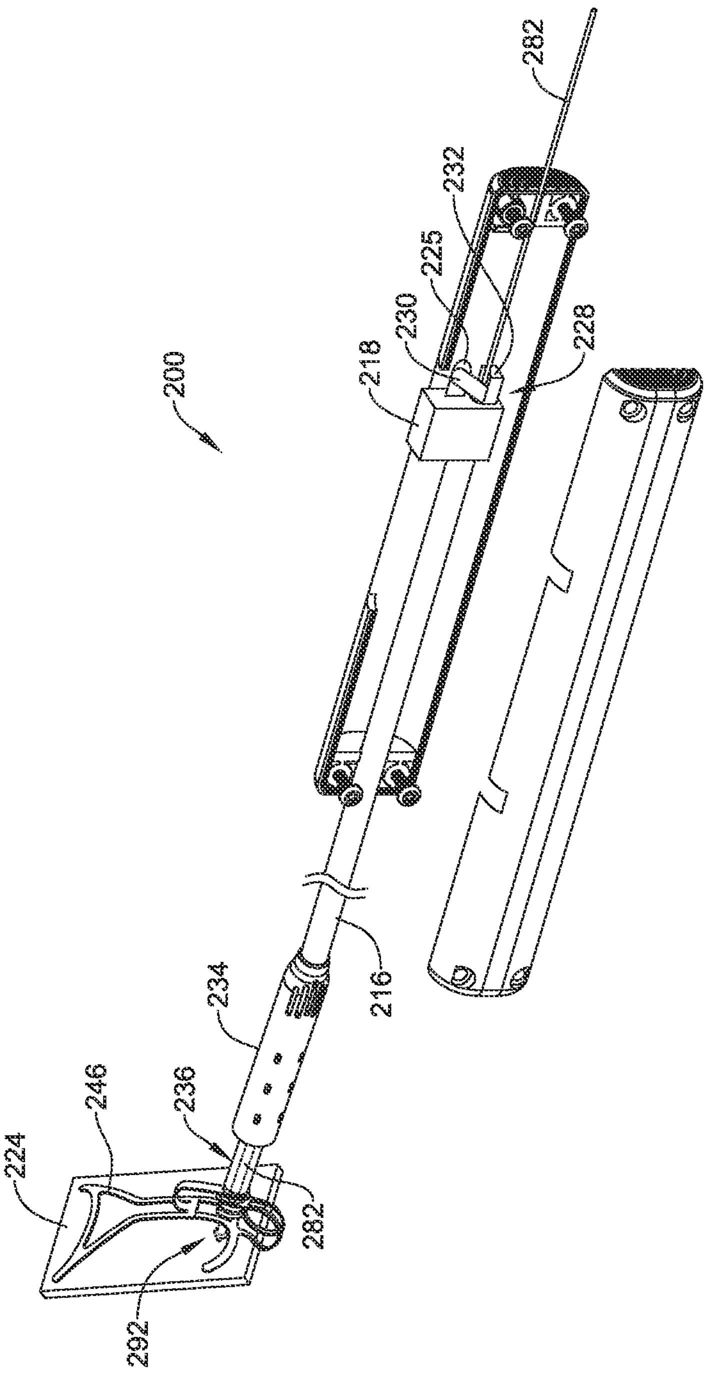
FIG. 15 is an exploded view of the example implant delivery system shown in FIG. 14.

FIGS. 14-15 illustrate a first step in utilizing the actuation member 218 to rotate the lever 230 relative to the block component 232, thereby freeing the tether 282. Specifically, FIG. 12 illustrates that the actuation member 218 has been translated proximally along the channel 220 to a position in which it is aligned with the second circumferential recess 223. It can be appreciated that the proximal translation of the actuation member 218 along the longitudinal axis may retract the outer shaft 216 such that the implant 224 and frame 246 are fully deployed out of the delivery sheath 234 (as shown in FIG. 14). Further, FIG. 14 illustrates a portion of the inner shaft 236 positioned distal to the delivery sheath 234, whereby the inner shaft 236 is coupled to the fully expanded frame 246 and implant 224. FIG. 14 further illustrates the tether 282 extending through the inner shaft 236. As discussed above, the tether 282 may be coupled to the tack member 292.

FIG. 15 illustrates a partially exploded view of the handle 212 shown in FIG. 14. As described above, FIG. 15 illustrates that the actuation member 218 has been translated proximally along the channel 220 to a position in which it is aligned with the second recess 223. Further, FIG. 15 illustrates that the actuation member 218 may include an engagement feature, such as a projection 225 (e.g., arm, fin) extending proximally away from the proximal end of the actuation member 218. As shown in FIG. 15, prior to being rotated about the longitudinal axis into the second recess 232, the engagement feature or projection 225 may be aligned with the lever 230. In other words, prior to being rotated into the second recess 232, the engagement feature or projection 225 may extend over the upper surface of the block component 232 and between the lever 230 and the inner surface of the handle 212.

Figure 16:
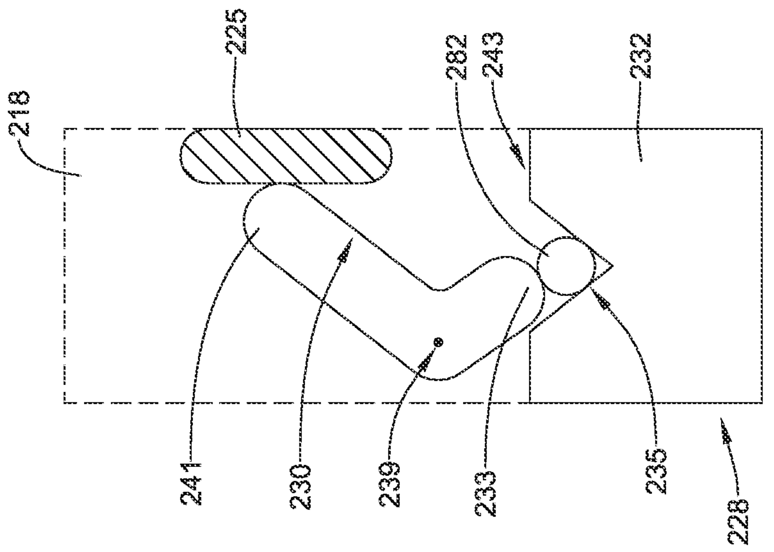
FIG. 16 is a schematic end view of the implant delivery system shown in FIG. 15.

For example, FIG. 16 illustrates an end view of the actuation member 218, lever 230 and block component 232 shown in FIG. 15. As described above, FIG. 16 illustrates the tether 282 positioned within the v-notch 235 of the block component 232. Additionally, FIG. 16 illustrates that the lever 230 may include a first end 233 which is biased to pinch the tether 282 within the v-notch 235 of the block component 232 or otherwise against a surface of the block component 232. Further, the lever 230 may also include a second end 241 which may be positioned adjacent to the projection 225 of the actuation member 218. As described above with respect to FIG. 15, prior to being rotated into the second recess 232, the projection 225 may extend over the upper surface 243 of the block component 232 and between the second end 241 of the lever 230 and the inner surface of the handle 212.

Figure 17:
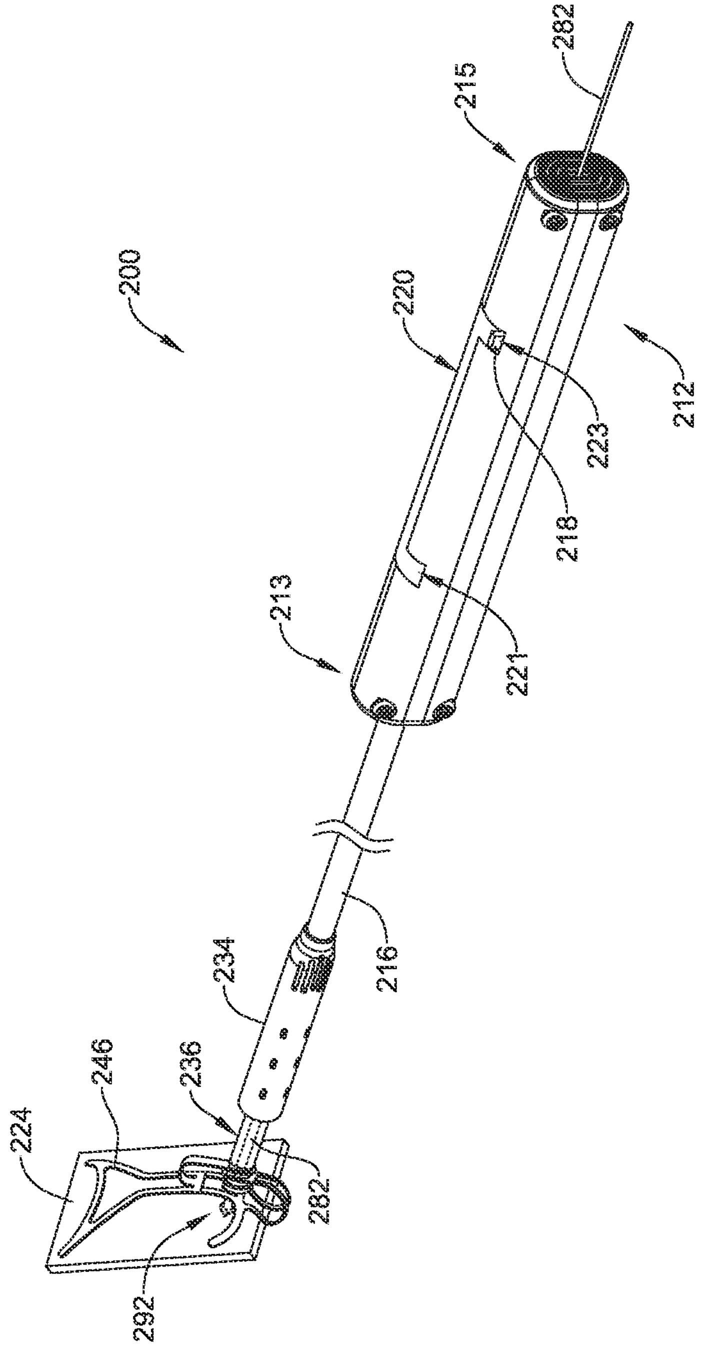
FIG. 17 is another perspective view of the example implant delivery system shown in FIG. 11.
Figure 18:
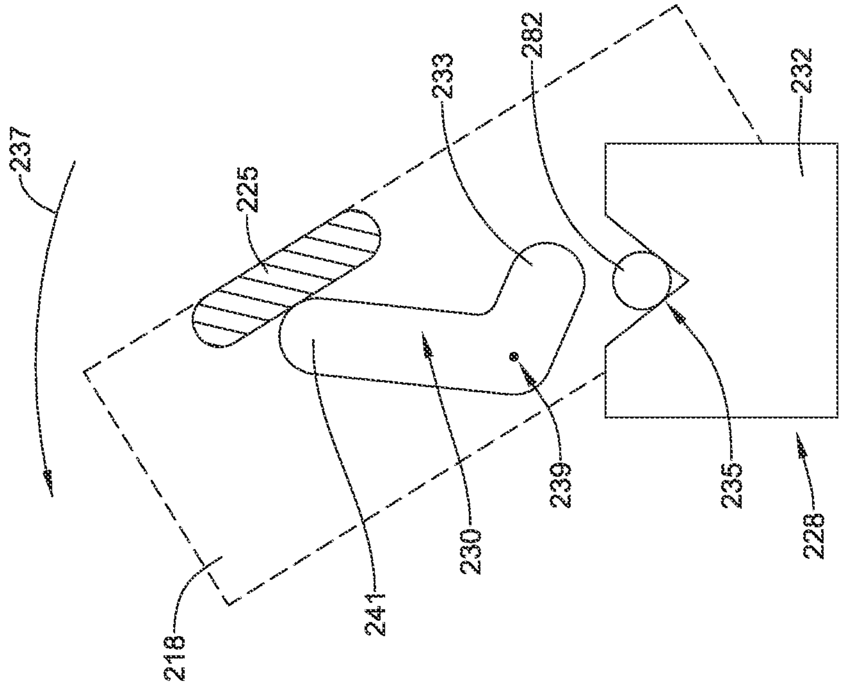
FIG. 18 is a schematic end view of the implant delivery system shown in FIG. 17.

FIGS. 17-18 illustrate a next step in actuating the actuation member 218 to rotate the lever 230 relative to the block component 232, thereby freeing the tether 282. Specifically, FIG. 17 illustrates the actuation member 218 being rotated about the longitudinal axis into the second recess 223. It can be appreciated that as the actuation member 218 is being rotated into the second recess 223, the outer shaft 216 remains retracted such that the implant 224 and frame 246 are fully deployed out of the delivery sheath 234. FIG. 17 further illustrates the tether 282 extending through the inner shaft 236. AS the actuation member 218 is rotated, the engagement feature (e.g., the projection 225 engages the lever 230 and causes the lever 230 to move from the engaged or locked position to the disengaged or unlocked position. Accordingly, in the configuration shown in FIG. 17, after the actuation member 218 is rotated into the second recess 223 and moved the lever 230 to the unlocked position, the tether 282 is free to move relative to the inner shaft 236, the outer shaft 216 and the handle 212.

FIG. 18 illustrates an end view of the position of the actuation member 218, the lever 230 and block component 232 shown in FIG. 17. Specifically, FIG. 18 illustrates an end view of the actuation member 218 rotated relative to the block component 232. Rotation of the actuation member 218 is depicted by the arrow 237. It can be appreciated from FIG. 18 that the rotation of the actuation member 218 causes the projection 225 to engage the second end 241 of the lever 230. Further, the engagement of the projection 225 with the second end 241 of the lever 230 pivots the lever 230 about the pivot point 239, thereby rotating the first end 233 of the lever 230 away from the tether 282. In this configuration, the tether 282 is free to move relative to the inner shaft 236, the outer shaft 216 and the handle 212.

Figure 19:
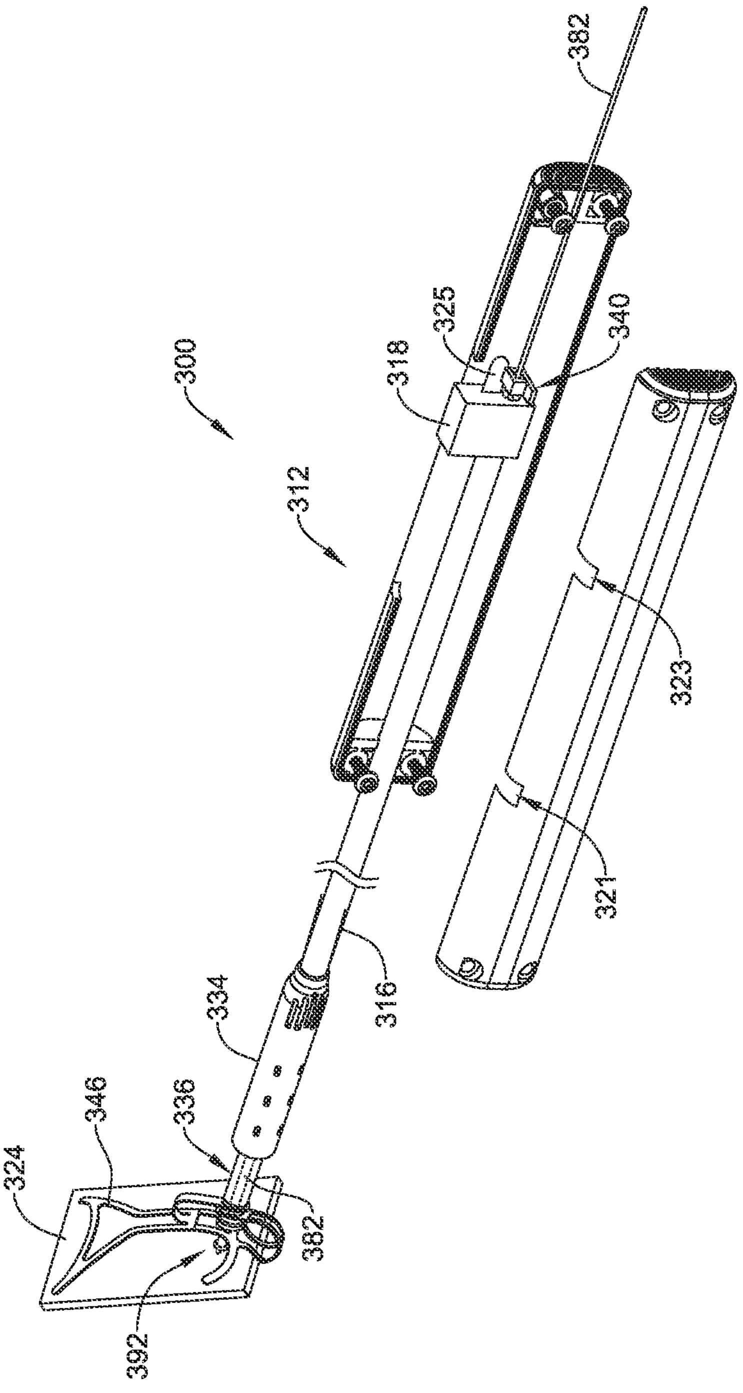
FIG. 19 is an exploded view of another example implant delivery system.

FIG. 19 illustrates another an implant delivery system 300. It can be appreciated that the implant delivery system 300 may be similar in form and function to other implant delivery systems described herein. It can be further appreciated that the configuration of the delivery system 300 shown in FIG. 19 may be similar to the delivery system 200 shown in FIG. 15.

For example, the implant delivery system 300 may include an outer shaft 316 coupled to a handle 312. Further, the distal end of the outer shaft 316 may include a delivery sheath 334. Like other delivery systems described herein, a frame 346 and an implant 324 may be positioned within the lumen of the delivery sheath 334 while being tracked to a target site. Further, as shown in FIG. 19, it can be appreciated that the actuation of the handle 312 may retract the outer shaft 316 to deploy the frame 346 and implant 324 out of the delivery sheath 334. Additionally, FIG. 19 further illustrates a tether 382 extending from a tack member 392, through the lumen of the inner shaft 336 (which extends through the lumen of the outer shaft 316), through an aperture located in the actuation member 318, through a tether clamp mechanism 340 and thereafter exit the proximal end of the handle 312. Similar to the embodiment above, further manipulation of the actuation member 318 after retracting the outer sheath 334 to expose the frame 346 and implant 324 may release or unclamp the tether member 382 from the handle 312. For example, further manipulation of the actuation member 318 may cause the actuation member 318 to move the tether clamp mechanism 328 from a locked or engaged position to an unlocked of disengaged position to release the tether member 382. In some instances, the actuation member 318 may be withdrawn proximally in a longitudinal direction (along the longitudinal axis) to retract the outer sheath 334, and thereafter, further manipulation of the actuation member 318 in a circumferential direction (e.g., rotated about the longitudinal axis) may cause the actuation member 318 to move the tether clamp mechanism 328 from a locked or engaged position to an unlocked of disengaged position to release the tether member 382.

FIG. 19 illustrates an actuation member 318 positioned adjacent to the tether clamp mechanism 340. Further, FIG. 19 illustrates that the actuation member 318 may include an engagement member, such as a projection 325 positioned adjacent to the tether clamp mechanism 340, configured to engage a surface of the tether clamp mechanism 340. Like the implant delivery system 200 described above, it can be appreciated that rotation of the actuation member 318 may engage the projection 325 with the tether clamp mechanism 340 to move the tether clamp mechanism from an engaged or locked position to a disengaged or unlocked position to free the tether 382.

Figure 20:
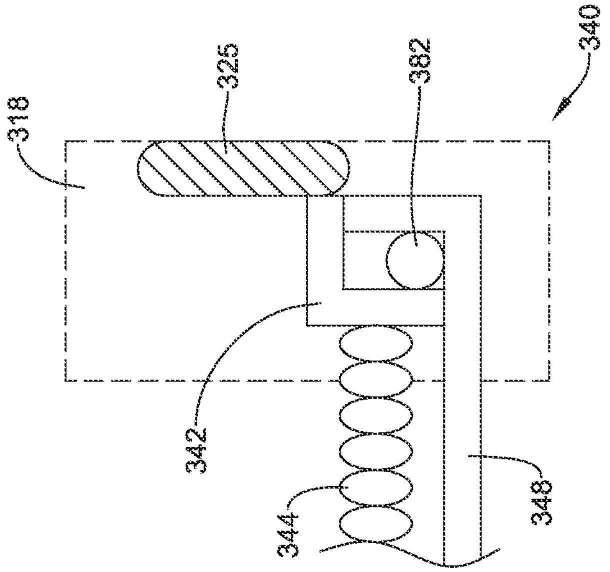
FIG. 20 is a schematic end view of the implant delivery system shown in FIG. 19.

For example, FIG. 20 illustrates an end view of the actuation member 318 relative to the tether clamp mechanism 340. FIG. 20 further illustrates the tether 382 positioned between a moving (e.g., sliding) component or block 342 (e.g., block, wedge, etc.) and a fixed component 348 (e.g., block, wedge, etc.) of the tether clamp mechanism 340. In some instances, the fixed component 348 may be an extension of the handle 312 (e.g., the fixed component may be a monolithic structure with the handle 312 and extend away from and inner surface thereof). It can be appreciated that the sliding component 342 may be free to move relative to the fixed component 348. For example, the moving or sliding component 342 may be free to shift closer to or away from the fixed component 348.

Additionally, FIG. 20 illustrates that the tether lock mechanism 340 may include a biasing member or spring 344. The spring 344 may include a first end coupled to the moving or sliding component 342 and a second end which may be coupled to an inner surface of the handle 312, for example. Accordingly, it can be appreciated that the spring 344 may exert a force of the moving or sliding component 342 which biases the sliding component 342 toward the fixed component 348 to thereby press the tether member 382 therebetween. It can be further appreciated that the force imparted by the spring 344 to the moving or sliding component 342 may pinch (e.g., secure, lock, hold) the tether 382 between the moving or sliding component 342 and the fixed component 348. Additionally, FIG. 20 illustrates that the projection 325 of the actuation member 318 may be aligned with the moving or sliding component 342. Like that described above with respect to the implant delivery system 200, prior to rotation of the actuation member 318, the tether 382 may be pinched or otherwise pressed between the moving or sliding component 342 and the fixed component 348, and may not be free to move relative to the inner shaft 336, the outer shaft 316 or the handle 312.

Figure 21:
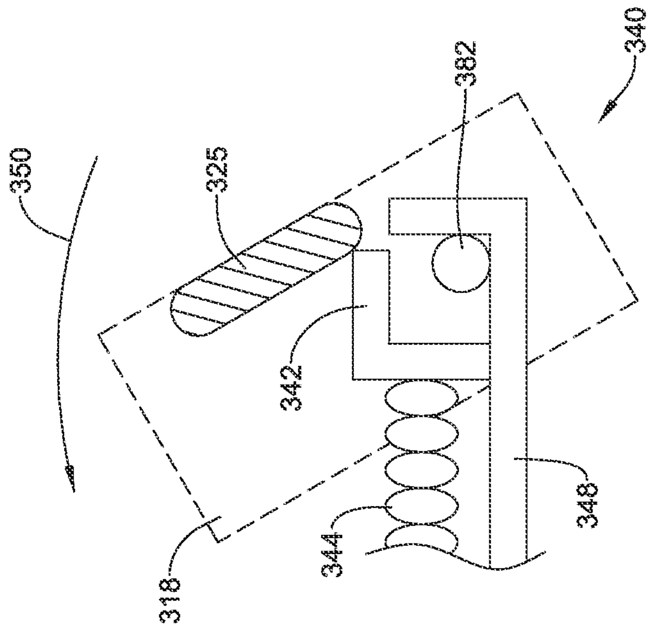
FIG. 21 is a schematic end view of the implant delivery system shown in FIG. 19 in a second position.

FIG. 21 illustrates the actuation member 318 rotating relative to the moving or sliding member 342 and the fixed component 348. Rotation of the actuation member 318 is depicted by the arrow 350. It can be appreciated that the actuation member 318 may be rotated about the longitudinal axis into a second recess of the handle 312. It can be further appreciated that as the actuation member 318 is rotated, the engagement feature or projection 325 of the actuation member 318 may engage the sliding component 342. Further, rotation of the projection 325 may engage the projection 325 with the moving or sliding component 342 and move the moving or sliding component 342 away from the fixed component 348, thereby freeing the tether 382. Accordingly, in the configuration shown in FIG. 21, after the actuation member 318 is rotated to the disengaged or unlocked position, the tether 382 is free to move relative to the inner shaft 336, the outer shaft 316 and the handle 312. However, it can be further appreciated that the outer shaft 316 remains retracted such that the implant 324 and the frame 346 are fully deployed out of the delivery sheath 334 when the actuation member 318 is rotated into the recess 323.

Figure 22:
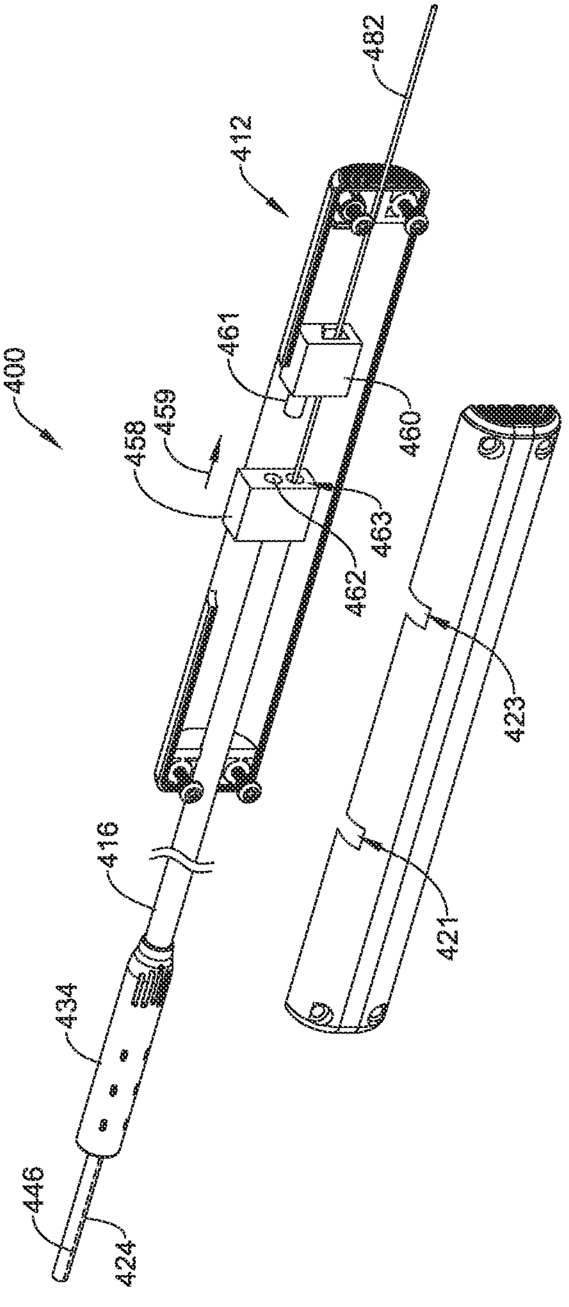
FIG. 22 is an exploded view of another implant delivery system.

FIG. 22 illustrates another an implant delivery system 400. It can be appreciated that the components of the implant delivery system 400 may be similar in form and function with other implant delivery systems described herein.

For example, the implant delivery system 400 may include an outer shaft 416 coupled to an actuation member 458, whereby the actuation member 458 is coupled to a handle 412. Further, the distal end of the outer shaft 416 may include a delivery sheath 434. Like other delivery systems described herein, a frame 446 and implant 424 may be positioned within the lumen of the delivery sheath 434 while being tracked to a target site. Further, as shown in FIG. 22, proximal translation 459 of the actuation member 458 may retract the outer shaft 416 to deploy the frame 446 and implant 424 out of the delivery sheath 434. Like FIG. 13 described above with respect to the implant delivery system 200, FIG. 22 illustrates that the actuation member 458 has been translated in a proximal direction along the handle 412 to a position in which it is approximately midway between the first recess 421 and the second recess 423 of the handle 412.

Further, in the position illustrated in FIG. 22, it can be appreciated that the outer shaft 416 has been retracted such that the implant 424 and frame 446 have been partially deployed out of the lumen of the delivery sheath 434.

FIG. 22 further illustrates that the implant delivery system 400 may also include a tether clamp mechanism 460 positioned proximal to the actuation member 458. The tether clamp mechanism 460 may include an engagement feature, such as a projection 461, which is designed to engage (e.g., insert into) a mating engagement feature, such as an aperture 462, located on the actuation member 458. While FIG. 22 illustrates that the tether clamp mechanism 460 may include a projection 461 designed to engage the aperture of the 462 of the actuation member 458, it is also contemplated that, in other examples, the actuation member 458 may include a projection designed to engage an aperture located on the tether clamp mechanism 460, for example. FIG. 22 further illustrates that the tether member 482 may extend through a portion of the tether clamp mechanism 460, such as between adjacent sidewalls of the tether clamp mechanism 460.

It can be appreciated that the tether clamp mechanism 460 may be utilized to fixedly secure the tether 482 from relative longitudinal movement relative to the inner shaft 436, the outer shaft 416 and the handle 412, when in a locked position. As will be described in greater detail below, the tether 482 may extend though the aperture of the tether clamp mechanism 460 before exiting the proximal end of the handle 412. Further, the tether clamp mechanism 460 may be biased in a first position in which it presses or pinches (e.g., locks, grips, holds) the tether 482 within the aperture of the tether clamp mechanism 460. Accordingly, and as will be described in further detail below, a portion of the tether clamp mechanism 460 may be moved (e.g., rotated) to free the tether 482. Rotation of the tether clamp mechanism 460 may be accomplished using the actuation member 458, as described below.

Figure 23:
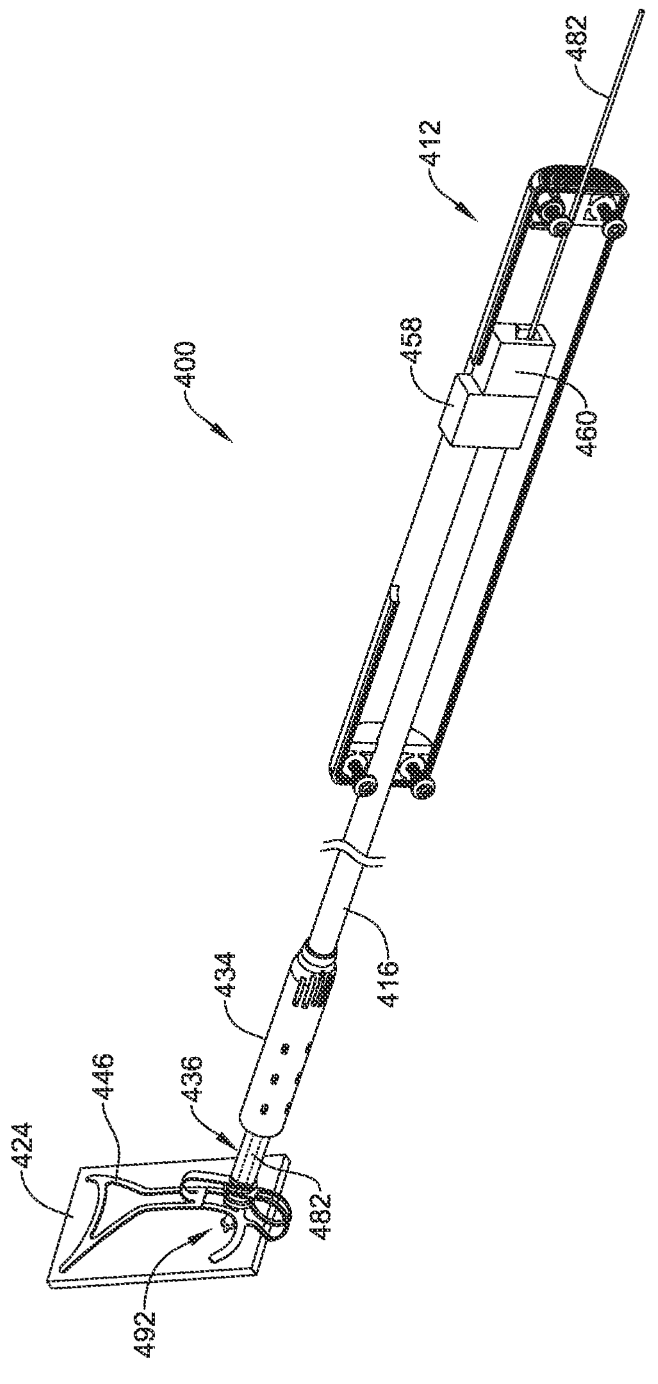
FIG. 23 is another exploded view of the implant delivery system shown in FIG. 22.

FIG. 23 illustrates the implant delivery device 400 shown in FIG. 14 whereby the actuation member 458 has been translated proximally to a position in which it is aligned with the second circumferential recess 423. Accordingly, it can be appreciated from FIG. 23 that the outer shaft 416 has been retracted such that the implant 424 and the frame 446 are fully deployed out of the delivery sheath 434. FIG. 23 further illustrates the tether 482 may extend from the tack member 492, through the lumen of the inner shaft 436 (extending through the outer shaft 416), through an aperture located in the actuation member 458, through the tether clamp mechanism 460 and thereafter exit the proximal end of the handle 412.

Further, FIG. 23 further illustrates that the actuation member 458 has engaged the tether clamp mechanism 460 in the retracted position, as described above. It can be appreciated that in the configuration shown in FIG. 23, the engagement feature (e.g., projection 461) of the tether clamp mechanism 460 has engaged the mating engagement feature of the actuation member 458 (e.g., has been inserted into the aperture 462 of the actuation member 458). In the configuration shown in FIG. 23, the tether member 482 may be pressed or pinched (e.g., locked, secured, held) within an aperture of the tether clamp mechanism 460. As described above, a portion of the tether clamp mechanism 460 may be rotated to free the tether 482. For example, a first side wall of the tether clamp mechanism 460 may be pivoted or deflected relative to an adjacent second side wall of the tether clamp mechanism 460 to widen a portion of the aperture through while the tether 482 extends. Rotation of the tether clamp mechanism 460 may be accomplished using the actuation member 458, as described below.

Figure 24:
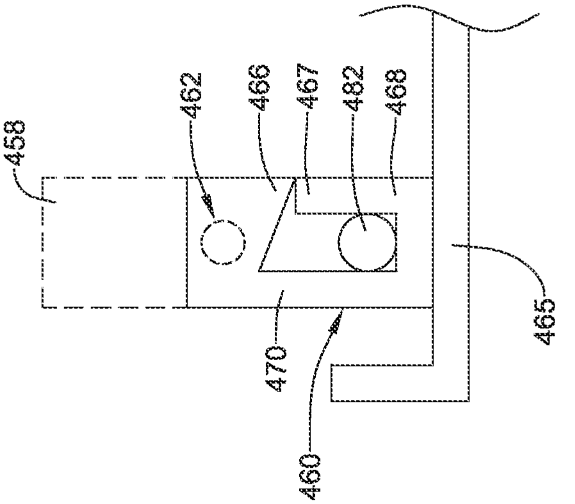
FIG. 24 is a schematic end view of the implant delivery system shown in FIG. 23.

For example, FIG. 24 illustrates an end view of the position of the actuation member 458 relative to the tether clamp mechanism 460 shown in FIG. 23. FIG. 24 further illustrates that the tether clamp mechanism 460 may include a first side wall 470 spaced away from a second side wall 468, whereby the tether 482 may be positioned between the first side wall 470 and the second side wall 468. Additionally, FIG. 24 illustrates that a bottom portion of the tether clamp mechanism 460 may connect the first side wall 470 to the second side 468 and may also be secured to a shelf 465. The shelf 465 may extend from an inner surface of the handle 412.

It can be appreciated that when positioned between the first side wall 470 and the second side wall 468, the tether 482 may be in a locked position, whereby the tether 482 may not be able to move relative to the inner shaft 436, the outer shaft 416 or the handle 412. Further, it can be appreciated that rotation of the first side wall 470 away from the second side wall 468 may free the tether 482 and permit it to move relative to the inner shaft 436, the outer shaft 416 or the handle 412.

Additionally, FIG. 24 illustrates that the tether clamp mechanism 460 may include an angled projection 466 which is designed to engage a first end 467 of the second side wall 468. Engagement of the projection 466 with the first end 467 of the second side wall 468 may provide an interference fit between the projection 466 and the first end 467 of the second side wall 468 which may need to be overcome to permit the first side wall 470 to rotate away from the second side wall 468. Additionally, FIG. 24 illustrates the aperture 462 of the actuation member 458, which may be designed to accept the projection 461 of the tether clamp mechanism 460, as described above.

Figure 25:
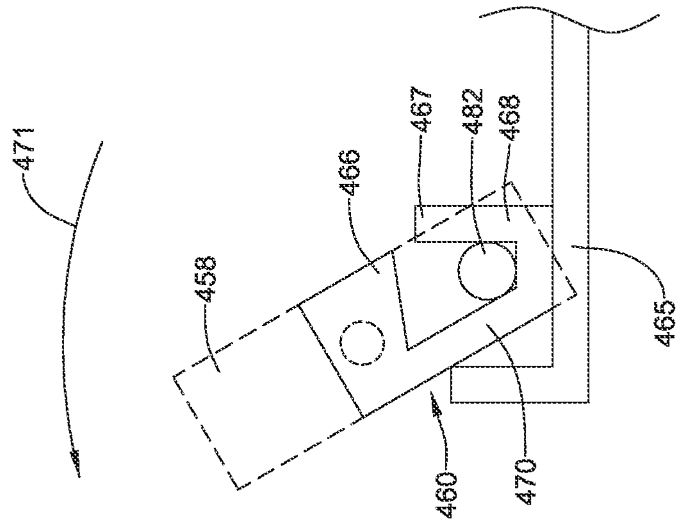
FIG. 25 is a schematic end view of the implant delivery system shown in FIG. 24 in a second position.

FIG. 25 illustrates the actuation member 458 rotating relative to the handle 412. Rotation of the actuation member 458 is depicted by the arrow 471 in FIG. 25. It can be appreciated that after withdrawing the actuation member 458 proximally to deploy the implant 424, the actuation member 458 may be rotated into a second recess 423 of the handle 412. It can be further appreciated that as the actuation member 458 is rotated, a portion of the tether clamp mechanism 460 may also rotate along with the actuation member 458 (as the tether clamp mechanism 460 is engaged with the actuation member 458 via the projection 461 of the tether clamp mechanism 460 extending into the aperture 462 of the actuation member 458). For example, FIG. 25 illustrates the first side wall 470 rotating away from the second side wall 468 as the actuation member 458 rotates into the second recess 423 of the handle 412. However, as discussed above, in order for the tether clamp mechanism 460 to rotate (along with the actuation member 458), the interference force established between the angled projection 466 and the first end 467 of the second side wall 468 may need to be overcome. However, if the interference force is overcome, and the tether clamp mechanism 460 is rotated, the tether 482 may be free to move relative to the inner shaft 436, the outer shaft 416 and the handle 412. It can be further appreciated that the outer shaft 416 remains retracted such that the implant 424 and the frame 446 are fully deployed out of the delivery sheath 434 while the actuation member 458 and the tether clamp mechanism 460 are rotated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An implant delivery system, the implant delivery system comprising:

an outer shaft having a proximal end, a distal end and a lumen extending therein;

an inner shaft including a proximal end and a distal end, the inner shaft extending within a least a portion of the lumen of the outer shaft;

a yoke immovably fixed to the distal end of the inner shaft; and an implant retainer coupled to the yoke, wherein the implant retainer is configured to capture an implant, the implant retainer including an upper beam immovably fixed to a lower beam, the implant retainer configured to capture the implant between the upper beam and the lower beam, and wherein the implant retainer is configured to pivot relative to the yoke.

2. The implant delivery system of claim 1, further comprising a spring component coupled to both the yoke and the implant retainer.

3. The implant delivery system of claim 2, wherein the spring component includes a first end and a second end, wherein the first end is fixedly attached to the yoke, and wherein the second end extends away from the yoke and is positioned within an internal bore located on the implant retainer.

4. The implant delivery system of claim 2, wherein the spring component includes a first end and a second end, wherein the first end is fixedly attached to the implant retainer, and wherein the second end extends away from the implant retainer and is positioned within an internal bore located on the yoke.

5. The implant delivery system of claim 2, wherein the spring component is configured to flex between a first position in which it is aligned with a longitudinal axis of the yoke and a second position in which it is offset from the longitudinal axis of the yoke.

6. The implant delivery system of claim 5, wherein the spring component is configured to bias the implant retainer in the second position after the implant is deployed from the lumen of the outer shaft.

7. The implant delivery system of claim 1, wherein the yoke includes a first longitudinal arm spaced away from a second longitudinal arm, and wherein the first longitudinal arm includes a first recess configured to accept a first projection positioned on the implant retainer, and wherein the second longitudinal arm includes a second recess configured to accept a second projection positioned on the implant retainer.

8. The implant delivery system of claim 7, wherein the first projection is configured to pivot within the first recess and wherein the second projection is configured to pivot within the second recess.

9. An implant delivery system, the implant delivery system comprising:

an elongate shaft including a proximal end, a distal end, and a longitudinal axis;

a yoke immovably fixed to the distal end of the elongate shaft;

an implant retainer pivotably coupled to the yoke about a rotational axis extending perpendicular to the longitudinal axis of the elongate shaft, and an implant removably coupled to the implant retainer;

wherein pivoting the implant retainer about the rotational axis moves a distal end of the implant away from the longitudinal axis such that the implant extends at an acute angle to the longitudinal axis;

wherein the implant retainer includes a plurality of flexible arms engaging an upper surface of the implant.

10. The implant delivery system of claim 9, wherein the plurality of flexible arms are deflected to fit within a lumen of a delivery sheath.

11. The implant delivery system of claim 10, wherein the plurality of flexible arms are configured to aid in unfolding the implant when deployed from the delivery sheath.

12. The implant delivery system of claim 9, further comprising a spring disposed between the yoke and the implant retainer, wherein the spring is configured to flex when the implant retainer is pivoted away from a non-deflected position to a deflected position.

13. The implant delivery system of claim 12, wherein the implant extends parallel to the longitudinal axis in the non-deflected position, and wherein the implant extends at an acute angle to the longitudinal axis in the deflected position.

* * * * *